(12) United States Patent
Horneman

(10) Patent No.: US 6,432,962 B2
(45) Date of Patent: Aug. 13, 2002

(54) BENZOPHENONES AS INHIBITORS OF IL-1β AND TNF-α

(75) Inventor: Anne Marie Horneman, Humlebæk (DK)

(73) Assignee: Leo Pharmaceutical Products Ltd. A/S, Ballerup (DK)

( * ) Notice: Subject to any disclaimer, the term of this patent is extended or adjusted under 35 U.S.C. 154(b) by 0 days.

(21) Appl. No.: 09/860,492

(22) Filed: May 21, 2001

Related U.S. Application Data

(60) Provisional application No. 60/205,579, filed on May 22, 2000.

(51) Int. Cl.$^7$ ................ C07D 213/02; A16K 31/44
(52) U.S. Cl. ............. 514/255.06; 514/256; 514/261; 514/310; 514/313; 514/352; 514/370; 514/394; 514/395; 546/146; 546/161; 546/312; 544/277; 544/311; 544/336; 548/161
(58) Field of Search .................. 546/146.161, 312; 514/310.313, 352, 370, 394.395, 255.06, 256.261; 544/277, 311, 336; 548/161, 307.04

(56) References Cited

FOREIGN PATENT DOCUMENTS

| | | |
|---|---|---|
| JP | 81-61259 | 10/1982 |
| WO | WO 98/32730 | 7/1998 |
| WO | WO 01/05744 | 1/2001 |
| WO | WO 01/05745 | 1/2001 |
| WO | WO 01/05746 | 1/2001 |
| WO | WO 01/05749 | 1/2001 |
| WO | WO 01/05751 | 1/2001 |
| WO | WO 01/42189 | 6/2001 |

OTHER PUBLICATIONS

Yamaguchi et al, Chemical Abstracts, vol. 116, No. 9, Abstract 95894v, p. 844, Mar. 2, 1992.*
Hussein et al, Iraqi J. Sci., 22(1):54–66 (1981).
Bhavsar et al, Man–Made Textiles in India, 30(6):275–276 (1987).
Bhavsar et al, Man–Made Textiles in India, 29(5):224–230 (1986).
Bhavsar et al, Man–Made Textiles in India, 28(11):425–431 (1985).

* cited by examiner

*Primary Examiner*—Zinna Northington Davis
(74) *Attorney, Agent, or Firm*—Birch, Stewart, Kolasch & Birch, LLP

(57) ABSTRACT

Heteroaryl aminobenzophenones of general formula I inhibit interleukin-1β and TNF-α and may therefore be useful in the therapy of inflammatory diseases and conditions.

50 Claims, No Drawings

BENZOPHENONES AS INHIBITORS OF IL-1β AND TNF-α

This application claims priority from Provisional application Ser. No. 60/205,579, filed May 22, 2000.

FIELD OF THE INVENTION

The present invention relates to a novel class of compounds, including heteroaryl aminobenzophenone derivatives, which show anti-inflammatory effects, to pharmaceutical compositions containing these compounds, and to their use in the treatment and prophylaxis of inflammatory diseases.

BACKGROUND OF THE INVENTION

A series of aminobenzophenones (e.g. 4-(2-amino-4-nitrophenylamino)benzophenone) have been described previously (Hussein, F. A. et al., Iraqi J. Sci., 22, 54–66 (1981)). In this publication, however, there is no description of any potential therapeutic use of such compounds. WO 98/32730 discloses aminobenzophenone inhibitors of interleukin 1β (IL-1β) and tumour necrosis factor α (TNF-α) secretion in vitro, and indicates the potential utility of these compounds in the treatment of inflammatory diseases in which the production of pro-inflammatory cytokines is involved in the pathogenesis, e.g. asthma, rheumatoid arthritis, psoriasis, contact dermatitis, and atopic dermatitis. Furthermore the A compounds disclosed in WO 98/32730 were tested in vivo for anti-inflammatory properties in the 12-O-tetradecanoylphorbol-13-acetate (TPA) induced murine chronic skin inflammation model (De Young, L. M. et al., Agents Actions 26, 335–341 (1989); Carlson, R. P. et al., Agents Actions 17, 197–204 (1985); Alford, J. G. et al., Agents Action 37, (1992); Stanley, P. L. et al., Skin Pharmacol. 4, 262–271 (1991)). In this chronic skin inflammation model the compounds had the same potency compared to the reference compound hydrocortisone.

It is the object of the present invention is to provide further pharmacologically active benzophenone derivatives which differ structurally from those disclosed in WO 98/32730.

SUMMARY OF THE INVENTION

It has surprisingly been found that novel benzophenone derivatives are potent inhibitors of interleukin 1β (IL-1β) and tumour necrosis factor α (TNF-α) secretion in vitro, making them potentially useful for the treatment and/or prevention of inflammatory diseases and other conditions in which the secretion and regulation of cytokines or more specifically interleukin 1β (IL-1β) and tumour necrosis factor α (TNF-α) are involved in the pathogenesis. The inhibition or downregulation of the cytokines is possibly due to an inhibition of MAP kinases, more specifically the p38 MAP kinase, a stress-activated protein which is an important element in the signal transduction pathway leading to the production of pro-inflammatory cytokines.

Accordingly, the present invention relates to a compound with the general formula I

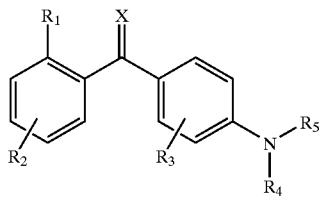

wherein $R_1$ is selected from the group consisting of halogen, haloalkyl, hydroxy, hydroxyalkyl, hydroxyalkyloxy, mercapto, cyano, carboxy, nitro, alkyl, alkenyl, alkynyl, cycloalkyl, cycloalkenyl, heterocycloalkyl, aryl, heteroaryl, aralkyl, alkylaryl, alkoxy, aralkoxy, alkylthio, alkoxycarbonyl, alkylcarbonyloxy, alkoxycarbonyloxy, alkylsulfonyloxy, alkyloxysulfonyl, alkylcarbonylamino, aminocarboaminoalkyl, aminosulfonyl, alkylsulfonylamino, alkanoyl, alkylcarbonyl, —$NR_9R_{10}$ or —$CONR_9R_{10}$, wherein $R_9$ and $R_{10}$ are the same or different and individually represent hydrogen, alkyl or aryl;

$R_2$ represents one or more, same or different substituents selected from the group consisting of hydrogen, halogen, haloalkyl, hydroxy, hydroxyalkyl, hydroxyalkyloxy, mercapto, cyano, carboxy, nitro, alkyl, alkenyl, alkynyl, cycloalkyl, cycloalkenyl, heterocycloalkyl, aryl, heteroaryl, aralkyl, alkylaryl, alkoxy, aralkoxy, alkylthio, alkoxycarbonyl, alkylcarbonyloxy, alkoxycarbonyloxy, alkylsulfonyloxy, alkyloxysulfonyl, alkylcarbonylamino, aminocarboaminoalkyl, aminosulfonyl, alkylsulfonylamino, alkanoyl, alkylcarbonyl, —$NR_9R_{10}$ or —$CONR_9R_{10}$, wherein $R_9$ and $R_{10}$ are the same or different and individually represent hydrogen, alkyl or aryl;

$R_3$ represents one or more, same or different substituents selected from the group consisting of hydrogen, halogen, haloalkyl, hydroxy, hydroxyalkyl, mercapto, cyano, nitro, alkyl, alkenyl, alkynyl, cycloalkyl, aryl, aralkyl, alkylaryl, alkoxy, aralkoxy, alkylthio, alkoxycarbonyl, alkylcarbonylamino, alkylcarbonyloxy, alkoxycarbonyloxy, alkylcarbonyl —$NR_9R_{10}$ or —$CONR_9R_{10}$, wherein $R_9$ and $R_{10}$ are the same or different and individually represent hydrogen, alkyl or aryl;

$R_4$ represents hydrogen, alkyl, alkenyl, alkynyl, cycloalkyl, cycloalkenyl, carboxy or aryl;

$R_5$ represents a heteroaromatic mono- or bicyclic ring system comprising 1–4 heteroatoms, except for triazine, said ring system being optionally substituted by hydrogen, halogen, haloalkyl, hydroxy, hydroxyalkyl, hydroxyalkyloxy, mercapto, cyano, carboxy, nitro, alkyl, alkenyl, alkynyl, cycloalkyl, cycloalkenyl, heterocycloalkyl, aryl, heteroaryl, aralkyl, alkylaryl, alkoxy, aralkoxy, alkylthio, alkoxycarbonyl, alkylcarbonyloxy, alkoxycarbonyloxy, alkylsulfonyloxy, alkyloxysulfonyl, alkylcarbonylamino, aminocarboaminoalkyl, aminosulfonyl, alkylsulfonylamino, alkanoyl, alkylcarbonyl, —$NR_9R_{10}$ or —$CONR_9R_{10}$, wherein $R_9$ and $R_{10}$ are the same or different and individually represent hydrogen, alkyl or aryl;

X represents oxygen, sulphur, N—OH or $NR_{11}$ wherein $R_{11}$ is hydrogen or alkyl;

or pharmaceutically acceptable salts hydrates, solvates or esters thereof as well as N-oxides wherein an N-atom of $R_5$ is oxidised.

DETAILED DESCRIPTION OF THE INVENTION

Definitions

In the present context, the term "alkyl" is intended to indicate a univalent radical derived from straight or branched alkane by removing a hydrogen atom from any carbon atom. The alkyl chain typically comprises 1–10 carbon atoms, in particular 1–6 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, pentyl, isopentyl, hexyl and isohexyl.

The term "haloalkyl" is intended to indicate an alkyl radical as defined above substituted by one or more halogens such as chloro, fluoro, bromo or iodo.

The term "hydroxyalkyl" is intended to indicate an alkyl radical as defined above substituted by one or more hydroxy groups.

The term "alkoxy" is intended to indicate a radical of formula OR', wherein R' is alkyl as defined above, e.g. methoxy, ethoxy, propoxy, butoxy, etc.

The term "hydroxyalkyloxy" is intended to indicate an alkoxy group as defined above substituted by one or more hydroxy groups.

The term "alkenyl" is intended to indicate a mono-, di-, tri-, tetra- or pentaunsaturated alkane radical typically comprising 2–10 carbon atoms, in particular 2–6 carbon atoms, e.g. ethenyl, propenyl, butenyl, pentenyl or hexenyl. The term "alkynyl" is intended to indicate an alkane radical comprising 1–5 triple C—C bonds, the alkane chain typically comprising 2–10 carbon atoms, in particular 2–6 carbon atoms, such as ethynyl, propynyl, butynyl, pentynyl or hexynyl.

The term "alkoxycarbonyl" is intended to indicate a radical of formula —COOR' wherein R' is alkyl as defined above, e.g. methoxycarbonyl, ethoxycarbonyl, n-propoxycarbonyl, isopropoxycarbonyl, etc.

The term "cycloalkyl" is intended to indicate a saturated cycloalkane radical typically comprising 3–10 carbon atoms, in particular 3–8 carbon atoms, e.g. cyclopropyl, cyclobutyl, cyclopentyl or cyclohexyl. The term "cycloalkenyl" is intended to indicate mono-, di- tri- or tetraunsaturated cycloalkane radicals, e.g. cyclopropenyl, cyclobutenyl, cyclopentenyl or cyclohexenyl. The term "heterocycloalkyl" is intended to indicate a cycloalkane radical as defined above, comprising one or more heteroatoms selected from O, N, or S.

The term "aryl" is intended to include radicals of carbocyclic aromatic rings, in particular 5- or 6-membered rings, optionally fused bicyclic rings, e.g. phenyl or naphthyl. The term "heteroaryl" is intended to include radicals of heterocyclic aromatic rings, in particular 5- or 6-membered rings with 1–4 heteroatoms selected from O, S and N, or optionally fused bicyclic rings with 1–4 heteroatoms, e.g. pyridyl, quinolyl, isoquinolyl, indolyl, tetrazolyl, thiazolyl, imidazolyl, pyrazolyl, oxazolyl, isoxazolyl, thienyl, pyrazinyl, isothiazolyl, benzimidazolyl and benzofuranyl.

The term "alkylcarbonyloxy" refers to a radical of formula R'—COO—, wherein R' is alkyl as indicated above. The term "alkoxycarbonyloxy" refers to a radical of formula R'O—COO—, wherein R' is alkyl as defined above. The term "alkylsulfonyloxy" refers to a radical of formula R'—(SO$_2$)—O—, wherein R' is alkyl as defined above. The term "alkyloxysulfonyl" refers to a radical of formula R'O—(SO$_2$)—, wherein R' is alkyl as defined above.

The term "aralkyl" is intended to indicate an aromatic ring with an alkyl side chain as defined above, e.g. benzyl. The term "alkylaryl" is intended to indicate an alkyl radical as defined above comprising an aromatic side chain.

The term "halogen" is intended to indicate fluoro, chloro, bromo or iodo. The term "alkylthio" is intended to indicate a radical of the formula —SR, where R is alkyl as defined above and includes methylthio, ethylthio, n-propylthio, and 2-propylthio.

The term "alkylamino" is intended to indicate a radical of the formula —NHR or —NR$_2$, where R is alkyl as defined above having from 1–6 carbon atoms and includes, for example, methylamino, dimethylamino, di-(n-propyl) amino, and n-butyl(ethyl)amino.

The term "carbamoyl" is intended to indicate the group —OCONH$_2$, —OCONHR, and —OCONRR' where R and R' represent alkyl as defined above.

The term "pharmaceutically acceptable salt" is intended to indicate alkali metal or alkaline earth metal salts, for instance sodium, potassium, magnesium or calcium salts, as well as silver salts and salts with suitable organic or inorganic acids such as hydrochloric, hydrobromic, hydroiodic, sulfuric, nitric, phosphoric, acetic, lactic, maleic, phthalic, citric, propionic, benzoic, glutaric, gluconic, methanesulfonic, salicylic, succinic, tartaric, toluenesulfonic, sulfamic or fumaric acid.

The term "pharmaceutically acceptable esters" is intended to indicate easily hydrolysable esters such as alkanoyloxyalkyl, aralkanoyloxyalkyl, aroyloxyalkyl, e.g. acetoxymethyl, pivaloyloxymethyl, benzoyloxymethyl esters and the corresponding 1'-oxyethyl derivatives, or alkoxycarbonyloxyalkyl esters, e.g. methoxycarbonyloxymethyl esters and ethoxycarbonyloxymethyl esters and the corresponding 1'-oxyethyl derivatives, or lactonyl esters, e.g. phthalidyl esters, or dialkylaminoalkyl esters, e.g. dimethylaminoethyl esters. Easily hydrolysable esters include in vivo hydrolysable esters of the compounds of formula I. Such esters may be prepared by conventional methods known to persons skilled in the art, such as method disclosed in GB patent No. 1 490 852 incorporated herein by reference.

"p38 MAP kinase" is a stress-activated protein kinase existing in several isoforms (p38α, p38β, p38β2, p38γ and p38δ). The p38 MAP kinase is activated by different stimuli including heat, chemical, osmotic, pH and oxidative stress, growth factor withdrawal, high or low glucose and ultraviolet radiation. p38 is also stimulated by agents that mediate the initial physiological response to injury, infection and inflammation, such as LPS and pro-inflammatory cytokines IL-1β, TNF-α, FasL, CD40L and TGF-β. Like other MAP kinases, p38 is phosphorylated by kinases, including MKK3, MEK6 and MKK6, on a threonine and tyrosine in an activation loop (Thr-Xaa-Tyr) close to the ATP and substrate binding site. In turn, p38 phosphorylates and activates the serine-threonine protein kinases MAPKAP kinase-2, MAPKAP kinase-3, MAPKAP kinase-5, MNK-1 and MSK-1. It has been established that activation of p38 regulates cytokine biosynthesis in many cell types either directly by phosphorylating and activating transcription factors involved in the expression of cytokines or indirectly, e.g. by phosphorylating MSK-1 which, when activated, activates the transcription factor CREB. It has also been shown that certain pyridinyl imidazoles, e.g. SB203580, inhibit the production of IL-1β and TNF-α from LPS-treated human monocytes, are inhibitors of p38 kinase. It has therefore been concluded that p38 constitutes a potentially highly interesting target for the development of anti-inflammatory compounds (cf. J C Lee et al., *Immunopharmacology* 47, 2000, pp. 185–201 and references reviewed 1t therein; P R Young, "Specific Inhibitors of p38 MAP kinase" in *Signaling Networks and Cell Cycle Control: The Molecular Basis of Cancer and Other Diseases*, J S Gutkind (Ed.), Humana Press, Inc., Totowa, N.J., and references reviewed therein).

PREFERRED EMBODIMENTS OF THE INVENTION

In compounds of formula I,

- $R_1$ preferably represents a substituent selected from the group consisting of halogen, hydroxy, mercapto, trifluoromethyl, amino, $(C_1-C_6)$alkyl, $(C_2-C_6)$alkenyl, $(C_1-C_6)$alkoxy, $(C_1-C_6)$alkylthio, $(C_1-C_6)$alkylamino, $(C_1-C_6)$ alkoxycarbonyl, cyano, —$CONH_2$, phenyl, and nitro, in particular fluoro, chloro, bromo, hydroxy, trifluoromethyl, amino, $(C_1-C_3)$alkyl, $(C_2-C_3)$alkenyl, $(C_1-C_3)$alkoxy, $(C_1-C_3)$ alkoxycarbonyl, cyano, or —$CONH_2$;
- $R_2$ represents one or more, same or different substituents selected from the group consisting of hydrogen, halogen, hydroxy, mercapto, trifluoromethyl, amino, $(C_1-C_6)$alkyl, $(C_2-C_6)$alkenyl, $(C_1-C_6)$alkoxy, $(C_1-C_6)$alkylthio, $(C_1-C_6)$alkylamino, $(C_1-C_6)$ alkoxycarbonyl, cyano, —$CONH_2$, phenyl, and nitro; in particular hydrogen, fluoro, chloro, bromo, hydroxy, trifluoromethyl, amino, $(C_1-C_3)$alkyl, $(C_2-C_3)$aikenyl, $(C_1-C_3)$alkoxy, $(C_1-C_3)$ alkoxycarbonyl, cyano, or —$CONH_2$;
- $R_3$ represents one or more, same or different substituents selected from the group consisting of hydrogen, halogen, hydroxy, mercapto, trifluoromethyl, amino, $(C_1-C_6)$alkyl, $(C_2-C_6)$alkenyl, $(C_1-C_6)$alkoxy, $(C_1-C_6)$alkylthio, $(C_1-C_6)$alkylamino, $(C_1-C_6)$ alkoxycarbonyl, cyano, —$CONH_2$, phenyl, and nitro, in particular hydrogen, fluoro, chloro, bromo, hydroxy, trifluoromethyl, amino, $(C_1-C_3)$alkyl, $(C_2-C_3)$alkenyl, and $(C_1-C_3)$alkoxy;
- $R_4$ represents hydrogen, $(C_1-C_6)$alkyl, $(C_2-C_6)$ alkenyl, or $(C_3-C_6)$ cycloalkyl or cycloalkenyl, in particular hydrogen, $(C_1-C_4)$ alkyl, or $(C_2-C_4)$ alkenyl;
- X represents oxygen or NH.

In the mono- or bicyclic heteroaromatic ring system represented by $R_5$, the heteroatom(s) may be selected from N, S or O. Each ring preferably comprises 5 or 6 ring atoms. Examples of suitable heteroaromatic ring systems are selected from the group consisting of pyridyl, pyrazinyl, pyrimidinyl, quinolyl, isoquinolyl, quinazolinyl, pyridazinyl, phthalazinyl, purinyl, quinoxalyl, allopurinyl, benzofuranyl, isobenzofuranyl, benzimidazolyl, benzoxazolyl, benzothienyl, isobenzothienyl, benzothiazolyl, benzoisothiazolyl, benzotriazolyl, indolizinyl, isoindolyl, indolyl, indazolyl, triazolyl, oxazolyl, thiadiazolyl, thienyl, furyl, pyrrolyl, imidazolyl, pyrazolyl, thiazolyl, isothiazolyl or isoxazolyl.

$R_5$ is preferably selected from heteroaromatic ring systems comprising 1 or 2 nitrogen atoms, e.g. rings of the structures:

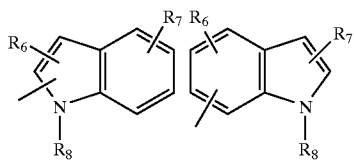

The $R_5$ ring-systems may optionally be oxidised to the corresponding N-oxides as exemplified below for the isoquinoline ring system:

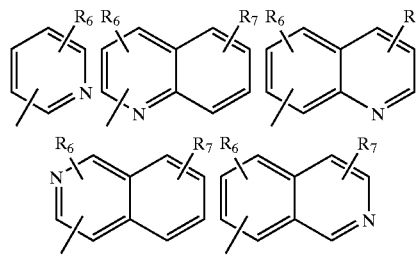

$R_6$ and $R_7$ represent one or more, same or different substituents selected from the group consisting of hydrogen, halogen, hydroxy, mercapto, trifluoromethyl, cyano, carboxy, carbamoyl, amino, nitro, $(C_1-C_{10})$alkyl, $(C_2-C_{10})$alkenyl, $(C_3-C_8)$ cycloalkyl or -cycloalkenyl, $(C_1-C_{10})$alkoxy, $(C_1-C_{10})$ alkylthio, $(C_1-C_{10})$ alkoxycarbonyl, and phenyl. In particular $R_6$ and $R_7$ represent one or more, same or different substituents selected from the group consisting of hydrogen, fluoro, chloro, bromo, hydroxy, trifluoromethyl, amino, $(C_1-C_6)$alkyl, $(C_2-C_6)$alkenyl, $(C_1-C_6)$alkoxy, $(C_1-C_6)$ alkoxycarbonyl, cyano, carboxy, and —$CONH_2$; and

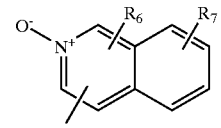

$R_8$ represents hydrogen, $(C_1-C_6)$alkyl, $(C_2-C_6)$alkenyl, or $(C_3-C_6)$cycloalkyl or -cycloalkenyl.

In compounds of formula I it is more preferred that

- $R_1$ represents a substituent selected from the group consisting of fluoro, chloro, bromo, hydroxy, methyl, and methoxy;
- $R_2$ represents one or more, same or different substituents selected from the group consisting of hydrogen, fluoro, chloro, bromo, hydroxy, trifluoromethyl, methyl, ethyl, and methoxy;
- $R_3$ represents one or more, same or different substituents selected from the group consisting of hydrogen, fluoro, chloro, bromo, hydroxy, methyl, and methoxy;
- $R_4$ represents hydrogen, methyl, or ethyl;
- $R_5$ is selected from the group consisting of substituted or non-substituted 3-pyridyl, 2-pyridyl, 3-quinolyl, 4-isoquinolyl, 4-indolyl, 5-indolyl, 6-indolyl and 7-indolyl moieties, and the corresponding N-oxides;
- $R_6$ and $R_7$ represent one or more, same or different substituents selected from the group consisting of hydrogen, fluoro, chloro, bromo, hydroxy, methyl, methoxy, cyano, and carboxy;

$R_8$ represents hydrogen, $(C_1-C_4)$alkyl, $(C_2-C_6)$alkenyl, such as allyl; and more preferably, $R_8$ represents hydrogen, methyl, ethyl, allyl, propyl, or t-butyl; and/or X represents oxygen.

The phenyl group of $R_1$, $R_2$, $R_3$, $R_6$ and $R_7$ may optionally be substituted, e.g. with hydroxy, amino, nitro, cyano or halogen, preferably fluoro or chloro.

Specific compounds of the invention are:

2-Chloro-2'-methyl-4-(4-pyridylamino)benzophenone (Compound 101), 2-Chloro-2'-methyl-4-(2-pyridylamino)benzophenone (Compound 102), 2-Chloro-2'-methyl-4-(5-nitro-2-pyridylamino)benzophenone (Compound 103), 4-(6-Amino-5-nitro-2-pyridylamino)-2-chloro-2'-methylbenzophenone (Compound 104), 6-Chloro-2-(3-chloro-4-(2-methylbenzoyl)phenylamino)isonicotinic acid (Compound 105), 4-(6-carbonitrile-2-pyridylamino)-2-chloro-2'-methylbenzophenone (Compound 106), 2-Chloro-2'-methyl-4-(3-pyridylamino)benzophenone (Compound 107), 2-Chloro-4-(5,6-diamino-2-pyridylamino)-2'-methylbenzophenone (Compound 108), 2-Chloro-2'-methyl-4-(3-nitro-2-pyridylamino)benzophenone (Compound 109), 4-(3-Amino-2-pyridylamino)-2-chloro-2'-methylbenzophenone (Compound 110), 4-(5-Amino-2-pyridylamino)-2-chloro-2'-methylbenzophenone (Compound 111), 2-Chloro-4-(4-isoquinolylamino)-2'-methylbenzophenone (Compound 114), t-Butyl 5-(3-chloro-4-(2-methylbenzoyl)phenylamino)nicotinoate (Compound 115, ) 2-Chloro-2'-methyl-4-(4-methyl-3-pyridylamino)benzophenone (Compound 116), 2-Chloro-2'-methyl-4-(6-methyl-3-pyridylamino)benzophenone (Compound 117), 4-(5-Bromo-3-pyridylamino)-2-chloro-2'-methylbenzophenone (Compound 118), 4-(5-Carbonitrile-3-pyridylamino)-2-chloro-2'-methylbenzophenone (Compound 119), 4-(3-Bromo-2-pyridylamino)-2-chloro-2'-methylbenzophenone (Compound 120), 2-Chloro-2'-methyl-4-(8-quinolylamino)benzophenone (Compound 121), 2-Chloro-4-(6-ethoxy-3-pyridylamino)-2'-methylbenzophenone (Compound 122), 4- (4-Bromo-1-isoquinolylamino)-2-chloro-2'-methylbenzophenone (Compound 123), 2-Chloro-2'-methyl-4-(2- methyl-5-trifluoromethyl-3-pyridylamino)benzophenone (Compound 124), 2-Chloro-2'-methyl-4-(3-quinolylamino) benzophenone (Compound 125), 2-Chloro-4-(4-ethoxy-3-pyridylamino)-2'-methylbenzophenone (Compound 126), 2-Chloro-4-(2-ethoxy-3-pyridylamino)-2'-methylbenzophenone (Compound 127), 2-Chloro-2'-methyl-4-(2-methyl-6-quinolylamino)benzophenone (Compound 129), 2-Chloro-4-(7-chloro-4-quinolylamino)-2'-methylbenzophenone (Compound 130), 2-Chloro-2'-methyl-4-(2-quinolylamino)benzophenone (Compound 131), 2-Chloro-2'-methyl-4-(4-quinolylamino) benzophenone(Compound 132), 2-Chloro-2'-methyl-4-(2-methyl-7-indolylamino) benzophenone (Compound 133), 2-Chloro-2'-methyl-4-(4-methyl-5-indolylamino)benzophenone (Compound 134), 2-Chloro-2',5'-dimethyl-4-(4-methyl-3-pyridylamino)benzophenone (Compound 135), 2-Chloro-2',5'-dimethyl-4-(4-isoquinolylamino) benzophenone (Compound 136), 2-Chloro-4-(4-isoquinolylamino)-2',4',5'-trimethylbenzophenone (Compound 137), 2,3'-Dichloro-2'-methyl-4-(4-methyl-3-pyridylamino)benzophenone (Compound 138), 2-Fluoro-2'-methyl-4-(4-methyl-3-pyridylamino) benzophenone (Compound 139), 2,4'-Dichloro-2'-methyl-4-(4-methyl-3-pyridylamino)benzophenone (Compound 140), 2-Chloro-4'-fluoro-4-(4-isoquinolylamino)-2'-methylbenzophenone (Compound 141), 4'-n-Butyl-2-chmoro-4-(4-isoquinolyl amino)-2'-methylbenzophenone (Compound 142), 2-Chloro-4-(5-isoquinolylamino)-2'-methylbenzophenone (Compound 143), 2-Chloro-4-(4-isoquinolylamino)-4'-methoxy-2'-methylbenzophenone (Compound 144), 2-Fluoro-4-(4-isoquinolylamino)-4'-methoxy-2'-methylbenzophenone (Compound 145), 2,4'-Dichloro-2'-methyl-4-(1-methyl-7-indolylamino)benzophenone (Compound 146), 2-Chloro-4-(1-methyl-7-indolylamino)-2',4',5'-trimethylbenzophenone (Compound 147), 2-Chloro-2',5'-dimethyl-4-(1-methyl-7-indolylamino)benzophenone (Compound 148), 2-Chloro-4-(3-ethoxy-4-isoquinolylamino)-2'-methylbenzophenone (Compound 149), 2-Chloro-4-(1-ethoxy-4-isoquinolylamino)-2'-methylbenzophenone (Compound 150), 4-(2-Benzoxazolylamino)-2-chloro-2'-methylbenzophenone (Compound 151), 4-(1-Methyl-2-benzimidazolylamino)-2-chloro-2'-methylbenzophenone (Compound 152), 4-(2-Benzothiazolylamino)-2-chloro-2'-methylbenzophenone (Compound 153), 2-Chloro-2'-methyl-4-(2-pyrimidylamino)benzophenone (Compound 154), 2-Chloro-2'-methyl-4-(7-methyl-purin-6-ylamino)benzophenone (Compound 155), 2-Chloro-2'-methyl-4-(2-methyl-5-benzothiazolylamino)benzophenone (Compound 156), 2-Chloro-2'-methyl-4-(pyrazin-2-ylamino) benzophenone (Compound 157), 2-Chloro-2'-methyl-4-(5-pyrimidylamino)benzophenone (Compound 158), 2-Chloro-2'-methyl-4-(5-nitro-2-thiazolylamino) benzophenone (Compound 159), 2-Chloro-2'-methyl-4-((4-methyl-3-nitro-(1,2,4-triazol-5-ylamino)) benzophenone (Compound 160)

and the N-oxides thereof wherein the nitrogen atom of the heterocyclic $R_5$ substituent is specifically oxidised.

More preferred compounds are:

2-Chloro-2'-methyl-4-(3-pyridylamino)benzophenone (Compound 107), 4-(3-Amino-2-pyridylamino)-2-chloro-2'-methylbenzophenone (Compound 110), 2-Chloro-4-(4-isoquinolylamino)-2'-methylbenzophenone (Compound 114), 2-Chloro-2'-methyl-4-(4-methyl-3-pyridylamino)benzophenone (Compound 116), 2-Chloro-2'-methyl-4-(6-methyl-3-pyridylamino)benzophenone (Compound 117), 4-(5-Bromo-3-pyridylamino)-2-chloro-2'-methylbenzophenone (Compound 118), 2-Chloro-2'-methyl-4-(8-quinolylamino)benzophenone (Compound 121), 2-Chloro-4-(6-ethoxy-3-pyridylamino)-2'-methylbenzophenone (Compound 122), 2-Chloro-2'-methyl-4-(3-quinolylamino) benzophenone (Compound 125), 2-Chloro-4-(4-ethoxy-3-pyridylamino)-2'-methylbenzophenone (Compound 126), 2-Chloro-2'-methyl-4-(1-methyl-7-indolylamino)benzophenone (Compound 133), 2-Chloro-2'-methyl-4-((1-methyl-5-indolylamino) benzophenone (Compound 134), 2-Chloro-2',5'-dimethyl-4-(4-methyl-3-pyridylamino)benzophenone (Compound 135) 2-Chloro-2',5'-dimethyl-4-(4-isoquinolylamino)benzophenone (Compound 136), 2-Chloro-4-(4-isoquinolylamino)-2',4',5'-trimethylbenzophenone (Compound 137), 2-Fluoro-2'- methyl-4-(4-methyl-3-pyridylamino)benzophenone (Compound 139), 2,4'-Dichloro-2'-methyl-4-(4-methyl-3-pyridylamino)benzophenone (Compound 140), 2-Chloro-4'-fluoro-4-(4-isoquinolylamino)-2'-methylbenzophenone (Compound 141), 2-Chloro-4-(5-isoquinolylamino)-2'-methylbenzophenone (Compound 143), 2-Chloro-4-(4-isoquinolylamino)-4'-methoxy-2'-methylbenzophenone (Compound 144), 2-Fluoro-4-(4-isoquinolylamino)-4'-methoxy-2'-methylbenzophenone (Compound 145), 2-Chloro-4-((3-ethoxy)-4-isoquinolylamino)-2'-methylbenzophenone (Compound 149), 2-Chloro-4-((1-ethoxy)-4-isoquinolylamino)-2'-methylbenzophenone (Compound 150)
and the N-oxides
2-Chloro-2'-methyl-4((2-pyridyl-N-oxide)amino)benzophenone (Compound 112), 2-Chloro-2'-methyl-4((3-pyridyl-N-oxide)amino)benzophenone (Compound 113), 2-Chloro-4((4-isoquinolyl-N-oxide)amino)-2'-methylbenzophenone (Compound 128), Compounds of formula Ia wherein X=S and wherein $R_1$, $R_2$, $R_3$, $R_4$, $R_5$, $R_6$, $R_7$ and $R_8$ are as indicated above, and compounds of formula Ib wherein X=N—OH and wherein $R_1$, $R_2$, $R_3$, $R_4$, $R_5$, $R_6$, $R_7$ and $R_8$ are as indicated above are also generally preferred.

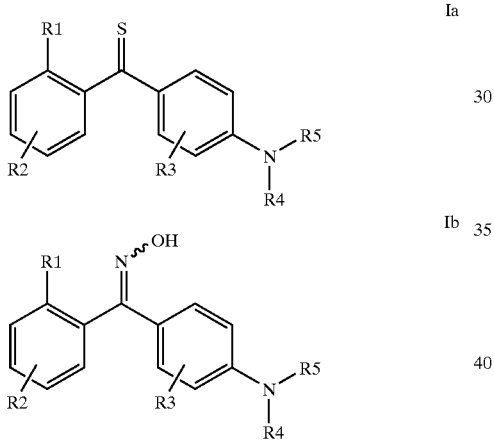

Specific compounds of formula Ia are:
2-Chloro-2'-methyl-4-(4-pyridylamino)thiobenzophenone, 2-Chloro-2'-methyl-4-(2-pyridylamino)thiobenzophenone, 2-Chloro-2'-methyl-4-(5-nitro-2-pyridylamino)thiobenzophenone, 4-(6-Amino-5-nitro-2-pyridylamino)-2-chloro-2'-methyl(thiobenzophenone), 6-Chloro-2-(3-chloro-4-(2-methylthiobenzoyl)phenylamino)isonicotinic acid, 4-(6-carbonitrile-2-pyridylamino)-2-chloro-2'-methyl(thiobenzophenone), 2-Chloro-2'-methyl-4-(3-pyridylamino)thiobenzophenone, 2-Chloro-4-(5,6-diamino-2-pyridylamino)-2'-methyl(thiobenzophenone), 2-Chloro-2'-methyl-4-(3-nitro-2-pyridylamino)thiobenzophenone, 4-(3-Amino-2-pyridylamino)-2-chloro-2'-methyl(thiobenzophenone), 4-(5-Amino-2-pyridylamino)-2-chloro-2'-methyl(thiobenzophenone), 2-Chloro-4-(4-isoquinolylamino)-2'-methyl(thiobenzophenone), t-Butyl 5-(3-chloro-4-(2-methylthiobenzoyl)phenylamino)nicotinoate, 2-Chloro-2'-methyl-4-(4-methyl-3-pyridylamino)thiobenzophenone, 2-Chloro-2'-methyl-4-(6-methyl-3-pyridylamino)thiobenzophenone, 4-(5-Bromo-3-pyridylamino)-2-chloro-2'-methyl(thiobenzophenone), 4-(5-Carbonitrile-3-pyridylamino)-2-chloro-2'-methyl(thiobenzophenone), 4-(3-Bromo-2-pyridylamino)-2-chloro-2'-methyl(thiobenzophenone), 2-Chloro-2'-methyl-4-(8-quinolylamino)thiobenzophenone, 2-Chloro-4-(6-ethoxy-3-pyridylamino)-2'-methyl(thiobenzophenone), 4-(4-Bromo-1-isoquinolylamino)-2-chloro-2'-methyl(thiobenzophenone), 2-Chloro-2'-methyl-4-(2-methyl-5-trifluoromethyl-3-pyridylamio)thiobenzophenone, 2-Chloro-2'-methyl-4-(3-quinolylamino)thiobenzophenone, 2-Chloro-4-(4-ethoxy-3-pyridylamino)-2'-methyl(thiobenzophenone), 2-Chloro-4-(2-ethoxy-3-pyridylamino)-2'-methyl(thiobenzophenone), 2-Chloro-2'-methyl-4-(2-methyl-6-quinolylamino)thiobenzophenone, 2-Chloro-2'-methyl-4-(2-quinolylamino)thiobenzophenone, 2-Chloro-4-(7-chloro-4-quinolylamino)-2'-methyl(thiobenzophenone), 2-Chloro-2'-methyl-4-(4-quinolylamino)thiobenzophenone, 2-Chloro-2'-methyl-4-(1-methyl-7-indolylamino)thiobenzophenone, and 2-Chloro-2'-methyl-4-(1-methyl-5-indolylamino)thiobenzophenone, 2-Chloro-2',5'-dimethyl-4-(4-methyl-3-pyridylamino)thiobenzophenone, 2-Chloro-2',5'-dimethyl-4-(4-isoquinolylamino)thiobenzophenone, 2-Chloro-4-(4-isoquinolylamino)-2',4',5'-trimethyl(thiobenzophenone), 2,3'-Dichloro-2'-methyl-4-(4-methyl-3-pyridylamino)thiobenzophenone, 2-Fluoro-2'-methyl-4-(4-methyl-3-pyridylamino)thiobenzophenone, 2,4'-Dichloro-2'-methyl-4-(4-methyl-3-pyridylamino)thiobenzophenone, 2-Chloro-4'-fluoro-4-(4-isoquinolylamino)-2'-methyl(thiobenzophenone), 4'-n-Butyl-2-chloro-4-(4-isoquinolylamino)-2'-methyl(thiobenzophenone), 2-Chloro-4-(5-isoquinolylamino)-2'-methyl(thiobenzophenone), 2-Chloro-4-(4-isoquinolylamino)-4'-methoxy-2'-methyl(thiobenzophenone), 2-Fluoro-4-(4-isoquinolylamino)-4'-methoxy-2'-methyl(thiobenzophenone), 2,4'-Dichloro-2'-methyl-4-(1-methyl-7-indolylamino)thiobenzophenone, 2-Chloro-4-(1-methyl-7-indolylamino)-2',4',5'-trimethyl(thiobenzophenone), 2-Chloro-2',5'-dimethyl-4-(1-methyl-7-indolylamino)thiobenzophenone, 2-Chloro-4-(3-ethoxy-4-isoquinolylamino)-2'-methyl(thiobenzophenone), 2-Chloro-4-(1-ethoxy-4-isoquinolylamino)-2'-methyl(thiobenzophenone), 4-(2-Benzoxazolylamino)-2-chloro-2'-methyl(thiobenzophenone), 4-(1-Methyl-2-benzimidazolylamino)-2-chloro-2'-methyl(thiobenzophenone), 4-(2-Benzothiazolylamino)-2-chloro-2'-methyl(thiobenzophenone), 2-Chloro-2'-methyl-4-(2-pyrimidylamino)thiobenzophenone, 2-Chloro-2'-methyl-4-(2-methyl-purin-6-ylamino)thiobenzophenone, 2-Chloro-2'-methyl-4-(2-methyl-5-benzothiazolylamino)thiobenzophenone, 2-Chloro-2'-methyl-4-(pyrazin-2-ylamino)thiobenzophenone, 2-Chloro-2'-methyl-4-(5-pyrimidylamino)thiobenzophenone
and salts thereof with pharmaceutically acceptable acids, hydrates and solvates.

Specific compound of formula Ib are:
2-Chloro-2'-methyl-4-(4-pyridylamino)benzophenone oxime, 2-Chloro-2'-methyl-4-(2-pyridylamino)benzophenone oxime, 2-Chloro-2'-methyl-4-(5-nitro-2-pyridylamino)benzophenone oxime, 4-(6-Amino-5-nitro-2-pyridylamino)-2-chloro-2'- methylbenzophenone oxime, 6-Chloro-2-((3-chloro-4-((hydroxyimino)(2-methylphenyl)methyl))phenylamino)isonicotinic acid, 4-(6-carbonitrile-2-pyridylamino)-2-chloro-2'-methylbenzophenone oxime, 2-Chloro-2'-methyl-4-(3-pyridylamino) benzophenone oxime, 2-Chloro-4-(5,6-diamino-2-pyridylamino)-2'-methylbenzophenone oxime, 2-Chloro-2'-methyl-4-(3-nitro-2-pyridylamino) benzophenone oxime, 4-(3-Amino-2-pyridylamino)-2-chloro-2'-methylbenzophenone oxime, 4-(5-Amino-2-pyridylamino)-2-chloro-2'-methylbenzophenone oxime, 2-Chloro-4-(4-isoquinolylamino)-2'-methylbenzophenone oxime, t-Butyl 5-((3-chloro-4-((hydroxyimino) (2-methylphenyl)methyl))phenylamino)nicotinoate, 2-Chloro-2'-methyl-4-(4-methyl-3-pyridylamino)benzophenone oxime, 2-Chloro-2'-methyl-4-(6-methyl-3-pyridylamino) benzophenone oxime, 4-(5-Bromo-3-pyridylamino)-2-chloro-2'-methylbenzophenone oxime, 4-(5-Carbonitrile-3-pyridylamino)-2-chloro-2'-methylbenzophenone oxime, 4-(3-Bromo-2-pyridylamino)-2-chloro-2'-methylbenzophenone oxime, 2-Chloro-2'-methyl-4-(8-quinolylamino) benzophenone oxime, 2-Chloro-4-(6-ethoxy-3-pyridylamino)-2'-methylbenzophenone oxime, 4-(4-Bromo-1-isoquinolylamino)-2-chloro-2'-methylbenzophenone oxime, 2-Chloro-2'-methyl-4-(2-methyl-5-trifluoromethyl-3-pyridylamino) benzophenone oxime, 2-Chloro-2'-methyl-4-(3-quinolylamino)benzophenone oxime, 2-Chloro-4-(4-ethoxy-3-pyridylamino)-2'-methylbenzophenone oxime, 2-Chloro-4-(2-ethoxy-3-pyridylamino)-2'-methylbenzophenone oxime, 2-Chloro-2'-methyl-4-(2-methyl-6-quinolylamino)benzophenone oxime, 2-Chloro-2'-methyl-4-(2-quinolylamino) benzophenone oxime, 2-Chloro-4-(7-chloro-4-quinolylamino)-2'-methylbenzophenone oxime, 2-Chloro-2'-methyl-4-(4-quinolylamino) benzophenone oxime, 2-Chloro-2'-methyl-4-(1-methyl-7-indolylamino)benzophenone oxime, and 2-Chloro-2'-methyl-4-(1-methyl-5-indolylamino) benzophenone oxime, 2-Chloro-2',5'-dimethyl-4-(4-methyl-3-pyridylamino)benzophenone oxime, 2-Chloro-2',5'-dimethyl-4-(4-isoquinolylamino) benzophenone oxime, 2-Chloro-4-(4-isoquinolylamino)-2',4',5'-trimethylbenzophenone oxime, 2,3'-Dichloro-2'-methyl-4-(4-methyl-3-pyridylamino)benzophenone oxime, 2-Fluoro-2'-methyl-4-(4-methyl-3-pyridylamino)benzophenone oxime, 2,4'-Dichloro-2'-methyl-4-(4- methyl-3-pyridylamino) benzophenone oxime, 2-Chloro-4'-fluoro-4-(4-isoquinolylamino)-2'-methylbenzophenone oxime, 4'-n-Butyl-2-chloro-4-(4-isoquinolylamino)-2'-methylbenzophenone oxime, 2-Chloro-4-(5-isoquinolylamino)-2'-methylbenzophenone oxime, 2-Chloro-4-(4-isoquinolylamino)-4'-methoxy-2'-methylbenzophenone oxime, 2-Fluoro-4-(4-isoquinolylamino)-4'-methoxy-2'-methylbenzophenone oxime, 2,4'-Dichloro-2'-methyl-4-(1-methyl-7-indolylamino)benzophenone oxime, 2-Chloro-4-(1-methyl-7-indolylamino)-2',4',5'-trimethylbenzophenone oxime, 2-Chloro-2',5'-dimethyl-4-(1-methyl-7-indolylamino)benzophenone oxime, 2-Chloro-4-(3-ethoxy-4-isoquinolylamino)-2'-methylbenzophenone oxime, 2-Chloro-4-(1-ethoxy-4-isoquinolylamino)-2'-methylbenzophenone oxime, 4-(2-Benzoxazolylamino)-2-chloro-2'-methylbenzophenone oxime, 4-(1-Methyl-2-benzimidazolylamino)-2-chloro-2'-methylbenzophenone oxime, 4-(-2-Benzothiazolylamino)-2-chloro-2'-methylbenzophenone oxime, 2-Chloro-2'-methyl-4-(2-pyrimidylamino)benzophenone oxime, 2-Chloro-2'-methyl-4-(7-methyl-purin-6-ylamino)benzophenone oxime, 2-Chloro-2'-methyl-4-(2-methyl-5-benzothiazolylamino)benzophenone oxime, 2-Chloro-2'-methyl-4-(pyrazin-2-ylamino)benzophenone oxime, 2-Chloro-2'-methyl-4-(5-pyrimidylamino) benzophenone oxime, and salts thereof with pharmaceutically acceptable acids, hydrates and solvates Compounds of general formula Ic

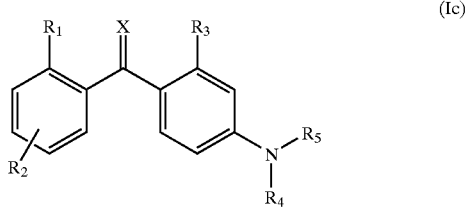

(Ic)

wherein $R_1$, $R_2$, $R_4$, $R_5$, $R_6$, $R_7$, $R_8$ and X are as indicated above, and $R_3$ represents $(C_1-C_3)$alkyl, fluoro, chloro, bromo, methoxy, and hydroxy, and salts thereof with pharmaceutically acceptable acids, hydrates and solvates, are generally preferred.

In formula Ic, $R_1$ preferably represents methyl or halogen, more preferably F or Cl; $R_2$ represents one or more substituents, preferably hydrogen, halogen, $(C_1-C_3)$alkyl, methoxy or ethoxy, and $R_3$ represents methyl, methoxy or chloro.

Pharmacological Methods

To study the effect of the compound of the present invention in vitro the inhibition of the IL-1β and TNF-α secretion was measured using the following procedure:

Cytokine production was measured in the media from lipopolysaccharide (LPS) stimulated peripheral blood mononuclear cells. The mononuclear cells were isolated from human peripheral blood by Lymphoprep® (Nycomed, Norway) fractionation and suspended in RPMI 1640 (growth medium) with foetal calf serum (FCS, 2%), at a concentration of $5 \times 10^5$ cells/ml. The cells were incubated in 24-well tissue culture plates in 1 mL aliquots. Test compounds were dissolved in dimethylsulfoxide (DMSO, 10 mM) and were diluted with the medium. Compounds were added to the cells for 30 minutes, then LPS (1 mg/mL final concentration) was added. The plates were incubated for 18 hours, and the concentration of IL-1β and TNF-α in the medium was determined by enzyme-linked immunosorbent assays. The median inhibitory concentrations ($IC_{50}$) of the compounds were calculated. The results are shown in Table 1.

The compounds of the present invention also show similar activities in the ability to inhibit PMN (polymorphonuclear) superoxide secretion which is also indicative of potentially useful anti-inflammatory drugs. The compounds were tested using the following procedure:

Human polymorphonuclear (PMN) granulocytes were isolated from human blood by dextran sedimentation, Lymphoprep® fractionation and hypotonic lysis of contaminating erythrocytes.

Superoxide anion generation was measured as the superoxide dismutase inhibitable reduction of ferricytochrome C (Madhu, S. B. et al, Inflammation, 16, 241, (1992)). The cells were suspended in Hanks' balanced salt solution, and incubated for 10 minutes at 37° C. with test compounds. The cells were primed by the addition of TNF-α (3 ng/mL final concentration) for 10 minutes, and then ferricytochrome C, (final concentration 750 µg/mL), bovine serum albumin (BSA, final concentration 1 mg/mL) and formylmethionyl-leucyl-phenylalanine (fMLP, final concentration $10^{-7}$ M) were added for 3 minutes. The cells were chilled on ice, and were spun down. The optical densities in the cell-free supernatant was measured in a spectrophotometer. The median inhibitory concentration ($IC_{50}$) of the compounds was calculated. The results, together with log P of the testet compounds are shown in Table 1.

TABLE 1

Inhibition of cytokines and PMN-superoxide production in vitro by compounds of the present invention. The median inhibition concentration ($IC_{50}$, nM)

| Comp. No. | IL-1β | TNF-α | PMN-superoxide | Log P of the present invention |
|---|---|---|---|---|
| Comp. 114 | 31 | 5.0 | 15 | 4.2 |
| Comp. 128 | 15.8 | 3.1 | 12.6 | 4.4 |
| Ref. comp. | 13 | 7.1 | 5.0 | 4.9 |

Ref. comp.: (4-(2-aminophenylamino)-2-chloro-2'-methylbenzophenone, Compound 156 disclosed in WO 98/32730.

These results show that the compounds of the present invention are able to inhibit the production of IL-1β, TNF-α and PMN-superoxide, and showing a pharmacological activity comparable to a reference compound, thus making them potentially useful in the treatment of inflammatory diseases. The lower log P values of the compounds of the present invention reflects a lower lipophilicity, which indicate compounds with an improved bioavailability as compared to the reference compound.

p38α MAP Kinase Assay

Cell Culture

COS-1 cells (derived from African green monkey kidney fibroblast-like cell containing wild-type T antigen under control of the SV40 promotor) were obtained from ATCC (ATCC no. CRL-1650) and grown in growth medium (DMEM without phenolred, 10% FCS, 2 mM L-glutamine, 100U penicillin and 100 µg streptomycin/ml) at 37° C. with 5% $CO_2$. The cells were passaged twice a week by trypsination (0.25% trypsin, 1 mM EDTA in PBS) and were split 1:10. The medium was changed every second or third day. The cell line was regularly tested with the Mycoplasma PCR Primer Set (Stratagene) and found to be free of Mycoplasma. Tissue culture media, FCS, L-glutamine and penicilin and streptomycin are from Bribco BRL, Gaithersburg, Md., USA.

Transient Expression of COS-1 Cells

On day one COS-1 cells were seeded in 143 $cm^2$ petridish with a density of $2 \times 10^4$ cells/$cm^2$ in growth medium. At day 2 the cells were co-transfected with 5 µg (total) of experimental plasmid DNA, expressing the FLAG-p38α and FLAG-MKK6(EE). The plasmids were introduced into the COS-1 cells in serum-free medium using DOTAP™ (Boehringer-Mannheim, Mannheim, Germany). Plasmid DNA was prepared and purified using the QIAGEN EndoToxin-free Maxiprep-500 kit (Hilden, Germany). Briefly, DNA and DOTAP™ were mixed for exactly 15 min. at 37° C. in the $CO_2$ incubator. The transfection-mixture was hereafter transferred to a 15-mL falcon-tube and transfection-medium (DMEM with L-Glutamine and Pen./Strep. but without serum) was added to the transfection-mixture, followed by addition to the cell-monolayer. After 4 hours of incubation with DOTAP™ and plasmids, the medium containing double amount of serum was added to the cells bringing the final concentration of serum up to 10%. The cells were then incubated for 24 hours before kinase reaction.

Immunoprecipitation

After 24 hrs of incubation the reaction was stopped by putting the petridish on an ice-bath. The medium was aspirated, and the cell monolayer was washed once in ice-cold PBS (137 mM NaCl, 1.5 mM $KH_2PO_4$, 2.7 mM KCl, 8.1 mM $Na_2HPO_4.2H_2O$), and hereafter solubilised for 10 min. in 1.5 mL lysis buffer (50 mM HEPES, pH 7.5, 150 mM NaCl, 10 mM EDTA, 10 mM $Na_4P_2O_7$, 100 mM NaF, 2 mM $Na_3VO_4$, 1% Triton-X-100, Pefabloc 500 µM, Leupeptin 10 µg/µl, Aprotinin 10 µg/µl) was added. The cell-monolayer was scraped by a rubber-policeman, and transferred to an Eppendorf tube. The solubilised cells were clarified by centrifugation at 10.000×g for 10 min. at 4° C. The supernatant was transferred to 50 µl prewashed Protein G Sepharose beads in HNT-buffer (30 mM HEPES, pH 7.5, 30 mM NaCl, 0.1% Triton X-100) and were incubated with 2 µg/sample of monoclonal anti-FLAG™ M2 antibody (raised against the FLAG-epitope, $NH_2$-Asp-Tyr-Lys-Asp-Asp-Asp-Asp-Lys-COOH) for 1 hour at room temperature. The anti-FLAG M2 monoclonal antibody was obtained from Sigma (cat. no. F-3165). Approx. 60 µg protein of clarified cell lysate were added to the preadsorbed anti-FLAG™ antibodies on Protein G Sepharose beads and incubated for 90 min. at 4° C. in a blood sample mixer. After the immunoprecipitation period the Sepharose beads were washed twice in lysis buffer and twice in a kinase reaction buffer (25 mM HEPES pH 7.5, 10 mM magnesium acetate, 50 µM ATP).

Incubation of the Compounds with Purified p38α Kinase

The pre-washed immunoprecipitated anti-FLAG-p38 adsorbed on Protein G Sepharose beads was washed twice in 1×kinase-buffer (25 mM HEPES pH 7.5, 10 mM magnesium acetate, 50 µM ATP), and the supernatant was aspirated. The compounds were diluted in 1×kinase buffer at the appropriate concentration. The compounds were added to the washed immunoprecipitated and activated FLAG-p38 adsorbed on the Protein G Sepharose beads for 30 min. at 30° C. in a volume of 100 µl. Every 10 min. the Eppendorf tubes were tapped to ensure that the beads and the compounds were in the solution. After 30 min. incubation, the beads were spinned down and the supernatant was aspirated.

p38α MAP Kinase Reaction

The kinase reaction was started by adding 1 µg GST-ATF-2 substrate (Santa Cruz, LaJolla, Calif., USA, cat. no. sc-4114) together with 2 µCi γ-$^{32}$P-ATP in 1×kinase-buffer per sample. The reaction was allowed to proceed for 30 min. at 30° C., and it was stopped by adding 40 µl of 2×SDS-sample buffer to the kinase reaction. The samples were boiled, spinned down, and resolved on a 15% SDS-PAGE. The dried SDS-PAGE gel was exposed to a Phospho-Imager screen and the radioactive PHAS-1 bands were quantified by the STORM860 Phospho-Imager (Molecular Dynamics, Sunnyvale, Calif., USA) using the ImageQuaNT software.

The inhibition exhibited by compound 114 in this assay is shown in table 2 below:

TABLE 2

| Compound No. | IC$_{50}$ values for the inhibition of p38α MAP kinase, mean concentration (nM) |
|---|---|
| Compound 114 | 12.8 |
| Reference compound, SB 203580 | 1056.6 |

Reference compound SB 203580 is a widely used reference compound for p38α MAP kinase inhibition. The compound is commercially available at Calbiochem (Calbiochem-Novabiochem Lajolla, Calif., USA)

These results show, that the compounds of this invention are potent p38α MAP kinase inhibitors with an improved pharmacological activity compared to a reference compound, thus making them potentially useful in the treatment of inflammatory diseases.

To study the compounds of the present invention in vivo the 12-O-tetradecanoylphorbol-13-acetate (TPA) induced murine chronic skin inflammation model can be used (De Young, L. M. et al., *Agents Actions* 26, 335–341 (1989); Carlson, R. P. et al., *Agents Actions* 17, 197–204 (1985); Alford, J. G. et al., *Agents Action* 37, (1992); Stanley, P. L. et al., *Skin Pharmacol.* 4, 262–271 (1991)), cf. the description of method in WO 98/32730 hereby incorporated by reference. These results show that compounds of the present invention are of the same potency compared to known reference compounds, e.g. hydrocortisone with its known side effects, whereas the compounds of the present invention are well tolerated and are non-toxic. Some members of the present class of compounds show a very low absorption, thus making them especially useful in the treatment of various dermatological diseases. In general, they may be administered by e.g. oral, intravenous, intranasal, topically or transdermal routes.

Methods of Preparing Compounds of Formula I

The compounds of the present invention may be prepared in a number of ways well known to those skilled in the art of organic synthesis. The compounds of the present invention may be synthesised using the methods outlined below, together with methods known in the art of synthetic organic chemistry, or variations thereof as appreciated by those skilled in the art. Preferred methods include, but are not limited to, those described below.

The novel compounds of formula I, Ia, and Ib may be prepared using the reactions and techniques described in this section. The reactions are performed in solvents appropriate to the reagents and materials employed and are suitable for the transformations being effected. Also, in the synthetic methods described below, it is understood that all proposed reaction conditions, including choice of solvent, reaction atmosphere, reaction temperature, duration of experiment and work-up procedures, are chosen as standard conditions for that reaction, which should be readily recognised by one skilled in the art. It is understood by one skilled in the art of organic synthesis that the functionality present on various portions of the educt molecule must be compatible with the reagents and reactions proposed. Not all compounds of formula I falling into a given class may be compatible with some of the reaction conditions required in some of the methods described. Such restrictions to the substituents which are compatible with the reaction conditions will be readily apparent to one skilled in the art and alternate methods can be used.

The following abbreviations have been used throughout this specification: BINAP=racemic or non-racemic 2,2'-bis (diphenylphosphino)-1,1'-binaphthyl, CDCl$_3$=deuteriochloroform, DMF=N,N-dimethyl-formamide, DMSO-d$_6$=hexadeuterodimethylsulfoxide, DMSO=dimethylsulfoxide, EtOAc=ethyl acetate, Et$_2$O=diethylether, Pd$_2$(dba)$_3$=tris(dibenzylideneacetone) dipalladium(0), mCPBA=meta-chloroperbenzoic acid, MeOH=methanol, NaOt-Bu=sodium-tert-butoxide, KOt-Bu=potassium-tert-butoxide THF=tetrahydrofurane, TLC=thin layer chromatography.

SCHEME 1

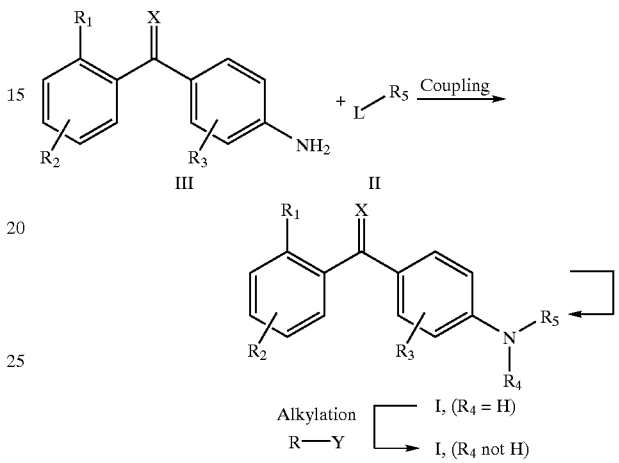

L: F, Cl, Br, I, or OSO$_2$CF$_3$
Y: Cl, Br, I, OSO$_2$R'
FGI: Functional group interconversion Compounds according to the present invention may be prepared by a process comprising coupling of an amine of the formula III with an bromide, iodide, fluoride, chloride or triflate with the formula II, as shown in Scheme 1, where R$_1$, R$_2$, R$_3$, R$_4$, R$_5$, and X are as defined in general formula I, except that any substituents or functional group which are potentially reactive in the coupling reaction may themselves be protected before the coupling reaction is performed and subsequently removed.

The coupling reaction is carried out using any of the methods for the formation of diphenylamines known to one skilled in the art of organic synthesis.

The preferred method is the palladium catalysed amination method which comprises coupling of an amine with an heteroarylhalogenide (or heteroaryltriflate) in the presence of a base, a suitable Pd source, and a suitable phosphine ligand in an inert solvent. (References: Wolfe, J. P.; Wagaw, S.; Buchwald, S. L.; *J. Am. Chem. Soc.*, (1996), 118, 7215–16; Wagaw, S.; Buchwald, S. L.; *J. Org. Chem.*, (1996), 61, 7240–41; Wolfe, J. P.; Buchwald, S. L.; *Tetrahedron Lett.*, (1997), 38, 6359–62; Hong. Y. et al., *Tetrahedron Lett.*, (1997), 38, 5607–10).

The palladium compound used in the process is not particularly limited, and as specific examples are palladium (II) acetate, palladium(II) chloride, palladium(II) bromide, dichlorobis(triphenylphosphine)palladium(II), tetrakis (triphenylphosphine)palladium(0), tris (dibenzylideneacetone)dipalladium(0). The preferred ligand include, but are not limited to, racemic or non-racemic 2,2'-bis(diphenylphosphino)-1,1'-binaphthyl (hereinafter referred to as BINAP), tri-o-tolylphosphine, tri-tert-butylphosphine, 1,1'-bis(diphenylphosphino)-ferrocene, bis [(2-diphenylphosphino)phenyl]ether (DPEphos), 2-dicyclohexylphosphanyl-2'-dimethylaminobiphenyl, 2-(di-tert-butylphosphino)biphenyl, and 9,9-dimethyl-4,6-bis(diphenylphosphino)xanthene (Xantphos). The amount of palladium and ligand used in this process is typically in the range 0.1 to 10% by mole relative to the amount of the aromatic halide (or triflate) used.

Especially NaOt-Bu and caesium carbonate ($Cs_2CO_3$) have proven to be the best bases in this process, but other bases may be used as well.

The reaction is typically performed at elevated temperature (80–120° C.) in inert solvents like 1,4-dioxane, toluene, benzene and tetrahydrofurane under an inert atmosphere like argon or nitrogen.

The coupling reaction may also be carried out by nucleophilic substitution of a heteroarylhalogenide with an amine, either in the presence of a base in a polar aprotic solvent, or without a solvent. The preferred base is KOt-Bu or NaH, but other bases may be used as well. The preferred solvent is dimethyl sulfoxide, but other solvents such as DMF may be used as well. The reaction is carried out at elevated temperature (120° C.–150° C.) for 12–24 h.

Compounds according to the present invention in which $R_4$ is not hydrogen may be prepared by a process comprising coupling of an amine of the formula I ($R_4$=H) with an alkylating agent, as shown in Scheme 1, where $R_1$, $R_2$, $R_3$, $R_5$, and X are as defined in general formula I, except that any substituents or functional group which are potentially reactive in the coupling reaction may themselves be protected before the coupling reaction is performed and subsequently removed.

Typically alkylating agents of the general formula R—Y include, but are not limited to, iodides (Y=I), bromides (Y=Br), chlorides (Y=Cl) and sulfonates (Y=$OSO_2R'$, where R' represents methyl, trifluoromethyl or 4-methylphenyl).

Compounds according to the present invention may in special cases be prepared by a simple functional group interconversion (FGI), meaning a standard process, known to those skilled in the art of organic synthesis, where a functional group in compounds with the general formula I is transformed into a different functional group in one or more synthetic steps, leading to a new compound with the general formula I. Examples of such processes are, but are not limited to, hydrolysis of an ester to give an acid under basic conditions; deprotection of an methylether to give an phenol by treatment with e.g. borontribromide ($BBr_3$); catalytic hydrogenation of an olefin to give an saturated hydrocarbon and reduction of a nitro group to give an amine.

Compounds according to the present invention with the general formula I were X=S may be prepared from the ketone (with the general formula I, C=O) by such a FGI process, by using one of the many thiocarbonylating reagent, known to those skilled in the art of organic synthesis. Examples of such thiocarbonylating reagents include, but are not limited to, phosphorous pentasulfide ($P_4S_{10}$), or Lawesson's reagent (2,4-bis(4-methoxyphenyl)-1,3,2,4-dithiaphosphetane-2,4-disulfide) or the like. Compounds accordingly to the present invention with the general formula I were X=N—OH may be prepared from the ketone (with the general formula I, C=O) by treatment with hydroxylamine, or a protected derivative thereof followed by deprotection, in an appropriate solvent like e.g. pyridine or methanol.

SCHEME 2

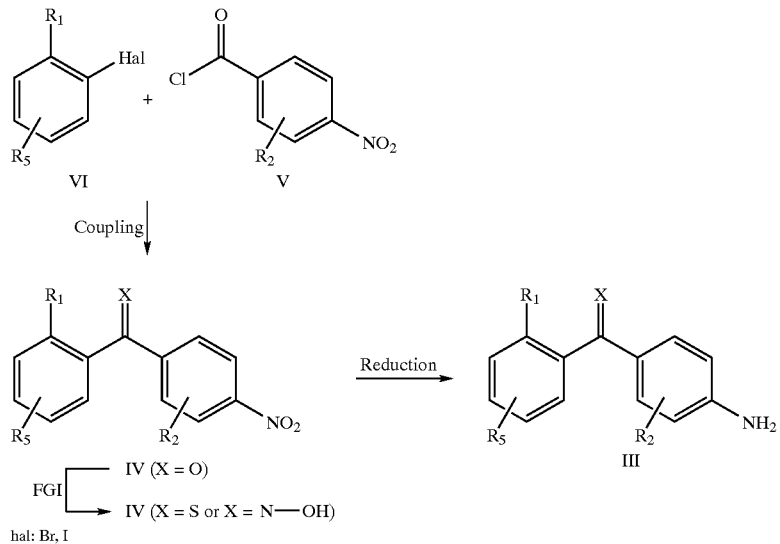

hal: Br, I

Compounds according to the present invention with the general formula III may be prepared by several methods known to those skilled in the art of organic synthesis. One useful sequence is shown in Scheme 2. The key step comprising coupling of a bromide (or iodide) with the general formula VI with an acid chloride with the general formula V to afford the benzophenone with the general formula IV. This compound IV may then be reduced to the corresponding amine with the general formula III by treatment with standard reducing agents. Examples of such reducing agents include, but are not limited to, stannous chloride dihydrate; hydrogen, ammonium formiate, or hydrazine hydrate and a catalytic amount of palladium on carbon. The coupling reaction is done by transforming the bromide (VI) into a reactive organometallic intermediate, e.g. by treatment with butyllithium to afford the lithium derivative or by treatment with magnesium to afford the magnesium derivative. The reactivity of this intermediate is then modulated by transmetalation to e.g. zinc, by treatment with $ZnCl_2$, $ZnBr_2$, or $ZnI_2$. This organozinc compound is then coupled with the acid chloride, with the general formula V, under the influence of a palladium 0) complex in catalytic amount. Examples of such catalyst include but are not particularly limited to tetrakis(triphenylphosphine)palladium(0), tetrakis(triphenylarsine)palladium(0), dichlorobis(triphenylphosphine)palladium(II), or benzylchlorobis(triphenylphosphine)palladium(II).

As shown in Scheme 2 compounds with the general formula IV (X=O) may be transformed by a FGI process to give compounds with the general formula IV (X=S or X=N—OH) as described above. This is only to illustrate the flexibility in the synthesis and in general the described sequence of processes is only one of many possible strategies for the synthesis of compound of the present invention. That is, it may be more advantageous in some cases to alter the sequence of the processes described above. The described sequence of processes is not considered as being limited for the preparation of the compounds of the present invention with the general formula I and alteration of the reaction sequence is an obvious alternative for those skilled in the art of organic synthesis.

Pharmaceutical Compositions

In another aspect, the invention relates to a pharmaceutical composition comprising, as an active component, a compound of formula I, Ia, Ib or Ic together with a pharmaceutically acceptable excipient or carrier. The term "pharmaceutically acceptable" is intended to indicate that the excipent or carrier included in the composition is compatible with the other ingredients and not toxic or otherwise deleterious to a patient to whom the composition is administered.

Pharmaceutical compositions of the invention may be in unit dosage form such as tablets, pills, capsules, powders, granules, elixirs, syrups, emulsions, ampoules, suppositories or parenteral solutions or suspensions; for oral, parenteral, opthalmic, transdermal, intra-articular, topical, pulmonal, nasal, buccal or rectal administration or in any other manner appropriate for the formulation of anti-inflammatory compounds and in accordance with accepted practices such as those disclosed in *Remington: The Science and Practice of Pharmacy.* $19^{th}$ Ed., Mack Publishing Company, 1995. The term "unit dosage" is intended to indicate a unitary, i.e. a single dose which is capable of being administered to a patient, and which may be readily handled and packed, remaining as a physically and chemically stable unit dose comprising either the active component as such or a mixture of it with solid or liquid pharmaceutical excipients or carriers. In the composition of the invention, the active component may be present in an amount of from about 0.1–100% by weight of the composition.

For oral administration in the form of a tablet or capsule, a compound of formula I may suitably be combined with an oral, non-toxic, pharmaceutically acceptable carrier such as ethanol, glycerol, water or the like. Furthermore, suitable binders, lubricants, disintegrating agents, flavouring agents and colourants may be added to the mixture, as appropriate. Suitable binders include, e.g., lactose, glucose, starch, gelatin, acacia gum, tragacanth gum, sodium alginate, carboxymethylcellulose, polyethylene glycol, waxes or the like. Lubricants include, e.g., sodium oleate, sodium stearate, magnesium stearate, sodium benzoate, sodium acetate, sodium chloride or the like. Disintegrating agents include, e.g., starch, methyl cellulose, agar, bentonite, xanthan gum or the like.

For the preparation of solid compositions such as tablets, the active compound of formula I is mixed with one or more excipients, such as the ones described above, and other pharmaceutical diluents such as water to make a solid preformulation composition containing a homogenous mixture of a compound of formula I. The term "homogenous" is understood to mean that the compound of formula I is dispersed evenly throughout the composition so that the composition may readily be subdivided into equally effective unit dosage forms such as tablets or capsules. The preformulation composition may then be subdivided into unit dosage forms containing from about 0.05 to about 1000 mg, in particular from about 0.1 to about 500 mg, of the active compound of the invention.

Liquid formulations for either oral or parenteral administration of the compound of the invention include, e.g., aqueous solutions, syrups, aqueous or oil suspensions and emulsion with edible oils such as cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose or polyvinylpyrolidone.

For parenteral administration, e.g. intramuscular, intraperitoneal, subcutaneous or intravenous injection or infusion, the pharmaceutical composition preferably comprises a compound of formula I dissolved or solubilised in an appropriate, pharmaceutically acceptable solvent. For parenteral administration, the composition of the invention may include a sterile aqueous or non-aqueous solvent, in particular water, isotonic saline, isotonic glucose solution, buffer solution or other solvent conventionally used for parenteral administration of therapeutically active substances, in particular antiproliferative agents. The composition may be sterilised by, for instance, filtration through a bacteria-retaining filter, addition of a sterilising agent to the composition, irradiation of the composition, or heating the composition. Alternatively, the compound of the invention may be provided as a sterile, solid preparation, e.g. a freeze-dried powder, which is dissolved in sterile solvent immediately prior to use.

The composition intended for parenteral administration may additionally comprise conventional additives such as stabilisers, buffers or preservatives, e.g. antioxidants such as methylhydroxybenzoate or the like.

Compositions for rectal administration may be in the form of a suppository incorporating the active ingredient and a carrier such as cocoa butter, or in the form of an enema.

Compositions suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Compositions suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. For topical administration, the active component preferably comprises from 1% to 20% by weight of the composition, but the active ingredient may comprise as much as 50% w/w.

Compositions suitable for administration to the nasal or buccal cavity or for inhalation include powder, self-propelling and spray formulations, such as aerosols and atomizers. Compositions suitable for nasal or buccal administration may comprise 0.1% to 20% w/w. for example about 2% w/w of active ingredient.

The composition may additionally comprise one or more other active components conventionally used in the treatment of various inflammatory diseases and conditions. Examples of such additional active components may be selected from the group consisting of glucocorticoids, vitamin D and vitamin D analogues, antihistamines, platelet activating factor (PAF) antagonists, anticholinergic agents, methylxanthines, β-adrenergic agents, COX-2 inhibitors, salicylates, infomethacin, flufenamate, naproxen, timegadine, gold salts, penicillamine, serum cholesterol lowering agents, retinoids, zinc salts and salicylazosulfapyridine.

In a further aspect, the invention relates to the use of a compound of formula I for the preparation of a medicament for the treatment or prophylaxis of inflammatory diseases or conditions. In a still further aspect, the invention relates to a method of treating inflammatory diseases or conditions, the method comprising administering, to a patient in need thereof, an effective amount of a compound of formula I.

A suitable dosage of the compound of the invention will depend, inter alia, on the particular compound selected for the treatment, the route of administration, the age and condition of the patient, the severity of the disease to be treated and other factors well known to the practising physician. The compound may be administered either orally or parenterally according to different dosing schedules, e.g. daily or with weekly intervals. In general a single dose will be in the range from 0.01 to 400 mg/kg body weight, such as from 0.1 to 100 mg/kg body weight. The compound may be administered as a bolus (i.e. the entire daily dosis is administered at once) or in divided doses two or more times a day.

Inflammatory diseases or conditions contemplated for treatment with the present compounds are inflammatory diseases where modulation of cytokine expression and secretion may be mediated by MAP kinases such as the p38 MAP kinase as discussed above. Examples of inflammatory diseases or conditions believed to be mediated by the p38 MAP kinase are selected from the group consisting of asthma, allergy, arthritis, including rheumatoid arthritis, osteoarthritis and spondyloarthritis, gout, atherosclerosis, inflammatory bowel diease, Crohn's disease, proliferative and inflammatory skin disorders, such as psoriasis, atopic dermatitis and acne vulgaris, uveitis, sepsis, septic shock, AIDS related diseases and osteoporosis.

The treatment may additionally involve administration of one or more other anti-inflammatory active components such as glucocorticoids, vitamin D and vitamin D analogues, antihistamines, platelet activating factor (PAF) antagonists, anticholinergic agents, methylxanthines, β-adrenergic agents, COX-2 inhibitors, salicylates, infomethacin, flufenamate, naproxen, timegadine, gold salts, penicillamine, serum cholesterol lowering agents, retinoids, zinc salts and salicylazosulfapyridine.

The invention is further described in the following general procedures, preparations and examples which are not in any way intended to limit the scope of the invention as claimed.

EXAMPLES

General Procedures, Preparations and Examples

Specific examples of compounds of formula I are listed in Table 3. All melting points are uncorrected. For $^1$H and $^{13}$C nuclear magnetic resonance (NMR) spectra (300 MHz for $^1$H) chemical shift values (δ) (in ppm) are quoted, unless otherwise specified, for deuteriochloroform and hexadeuterodimethyl-sulfoxide solutions relative to internal tetramethylsilane (δ 0.00) or chloroform ($^1$H NMR δ 7.25, $^{13}$C NMR δ 76.81). The value for a multiplet (m), eventually defined as a doublet (d), triplet (t) or quartet (q) is given at the approximate mid point unless a range is quoted. A signal may also be defined as a singlet (s) or broad singlet (b). The organic solvents used were anhydrous. The term "chromatography" refers to column chromatography using the flash technique and was performed on silica gel.

TABLE 3

Compounds of General formula

| Comp. No. Example No. | X | $R_1$ | $R_2$ | $R_3$ | $R_4$ | $R_5$ | $R_6$ | $R_7$ |
|---|---|---|---|---|---|---|---|---|
| Comp. 101 Ex. 1 | O | CH$_3$ | H | 2-Cl | H | (pyridinyl structure) | H | — |
| Comp. 102 Ex. 2 | O | CH$_3$ | H | 2-Cl | H | (pyridinyl structure) | H | — |
| Comp 103 Ex. 3 | O | CH$_3$ | H | 2-Cl | H | Same as ex. 2 | 5-NO$_2$ | — |
| Comp. 104 Ex. 4 | O | CH$_3$ | H | 2-Cl | H | Same as ex. 2 | 5-NO$_2$, 6-NH$_2$ | — |
| Comp. 105 Ex. 5 | O | CH$_3$ | H | 2-Cl | H | Same as ex. 2 | 4-COOH, 6-Cl | — |
| Comp. 106 Ex. 6 | O | CH$_3$ | H | 2-Cl | H | Same as ex. 2 | 3-CN | — |

TABLE 3-continued

Compounds of General formula

| Comp. No. Example No. | X | $R_1$ | $R_2$ | $R_3$ | $R_4$ | $R_5$ | $R_6$ | $R_7$ |
|---|---|---|---|---|---|---|---|---|
| Comp. 107 Ex. 7 | O | $CH_3$ | H | 2-Cl | H | 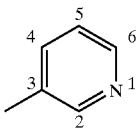 | H | — |
| Comp. 108 Ex. 8 | O | $CH_3$ | H | 2-Cl | H | Same as ex 2 | 5,6-di-$NH_2$ | — |
| Comp. 109 Ex. 9 | O | $CH_3$ | H | 2-Cl | H | Same as ex. 2 | 3-$NO_2$ | — |
| Comp. 110 Ex. 10 | O | $CH_3$ | H | 2-Cl | H | Same as ex. 2 | 3-$NH_2$ | — |
| Comp. 111 Ex. 11 | O | $CH_3$ | H | 2-Cl | H | Same as ex. 2 | 5-$NH_2$ | — |
| Comp. 112 Ex. 12 | O | $CH_3$ | H | 2-Cl | H | 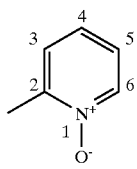 | H | — |
| Comp. 113 Ex. 13 | O | $CH_3$ | H | 2-Cl | H | 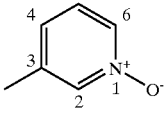 | H | — |
| Comp. 114 Ex. 14 | O | $CH_3$ | H | 2-Cl | H | 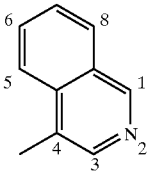 | H | H |
| Comp. 115 Ex. 15 | O | $CH_3$ | H | 2-Cl | H | 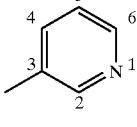 | 3-$COOC_4H_9$ | — |
| Comp. 116 Ex. 16 | O | $CH_3$ | H | 2-Cl | H | Same as ex. 7 | 4-$CH_3$ | — |
| Comp. 117 Ex. 17 | O | $CH_3$ | H | 2-Cl | H | Same as ex. 7 | 6-$CH_3$ | — |
| Comp. 118 Ex. 18 | O | $CH_3$ | H | 2-Cl | H | Same as ex. 7 | 5-Br | — |
| Comp. 119 Ex. 19 | O | $CH_3$ | H | 2-Cl | H | Same as ex. 7 | 5-CN | — |
| Comp. 120 Ex. 20 | O | $CH_3$ | H | 2-Cl | H | same as ex. 2 | 3-Br | — |
| Comp. 121 Ex. 21 | O | $CH_3$ | H | 2-Cl | H | 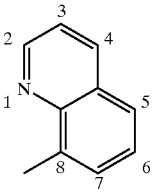 | H | H |

TABLE 3-continued

_Compounds of General formula_

| Comp. No. Example No. | X | R₁ | R₂ | R₃ | R₄ | R₅ | R₆ | R₇ |
|---|---|---|---|---|---|---|---|---|
| Comp. 122 Ex. 22 | O | CH₃ | H | 2-Cl | H | same as ex. 7 | 6-OC₂H₅ | — |
| Comp. 123 Ex. 23 | O | CH₃ | H | 2-Cl | H | 1-methylisoquinolin-4-yl (positions 1–8 labeled) | 4-Br | H |
| Comp. 124 Ex. 24 | O | CH₃ | H | 2-Cl | H | same as ex 7 | 2-CH₃, 5-CF₃ | — |
| Comp. 125 Ex. 25 | O | CH₃ | H | 2-Cl | H | 3-methylquinolin-? (positions 1–8 labeled) | H | H |
| Comp. 126 Ex. 26 | O | CH₃ | H | 2-Cl | H | same as ex. 7 | 4-OC₂H₅ | — |
| Comp. 127 Ex. 27 | O | CH₃ | H | 2-Cl | H | same as ex. 7 | 2-OC₂H₅ | — |
| Comp. 128 Ex. 28 | O | CH₃ | H | 2-Cl | H | 4-methylisoquinoline N-oxide (positions 1–8 labeled) | H | H |
| Comp. 129 Ex. 29 | O | CH₃ | H | 2-Cl | H | 6-methylquinolin-? (positions 1–8 labeled) | H | 2-CH₃ |
| Comp. 130 Ex. 30 | O | CH₃ | H | 2-Cl | H | 4-methylquinolin-? (positions 1–8 labeled) | H | 7-Cl |
| Comp. 131 Ex. 31 | O | CH₃ | H | 2-Cl | H | 2-methylquinolin-? (positions 1–8 labeled) | H | H |

TABLE 3-continued

Compounds of General formula

| Comp. No. Example No. | X | R₁ | R₂ | R₃ | R₄ | R₅ | R₆ | R₇ |
|---|---|---|---|---|---|---|---|---|
| Comp. 132 Ex. 32 | O | CH₃ | H | 2-Cl | H | same as ex. 30 | H | H |
| Comp. 133 Ex. 33 | O | CH₃ | H | 2-Cl | H | 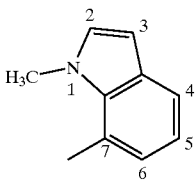 | H | H |
| Comp. 134 Ex. 34 | O | CH₃ | H | 2-Cl | H | 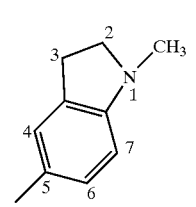 | H | H |
| Comp. 135 Ex. 35 | O | CH₃ | 5-CH₃ | 2-Cl | H | Same as ex. 7 | 4-CH₃ | — |
| Comp. 136 Ex. 36 | O | CH₃ | 5-CH₃ | 2-Cl | H | Same as ex. 14 | H | H |
| Comp. 137 Ex. 37 | O | CH₃ | 4-CH₃, 5-CH₃ | 2-Cl | H | Same as ex. 14 | H | H |
| Comp. 138 Ex. 38 | O | CH₃ | 3-Cl | 2-Cl | H | Same as ex. 7 | 4-CH₃ | — |
| Comp.139 Ex. 39 | O | CH₃ | H | 2-F | H | Same as ex. 7 | 4-CH₃ | — |
| Comp. 140 Ex. 40 | O | CH₃ | 4-Cl | 2-Cl | H | Same as ex. 7 | 4-CH₃ | — |
| Comp. 141 Ex. 41 | O | CH₃ | 4-F | 2-Cl | H | Same as ex. 14 | H | H |
| Comp. 142 Ex. 42 | O | CH₃ | 4-n-butyl | 2-Cl | H | Same as ex. 14 | H | H |
| Comp. 143 Ex. 43 | O | CH₃ | H | 2-Cl | H | 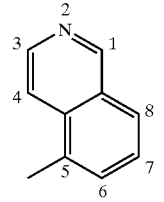 | H | H |
| Comp. 144 Ex. 44 | O | CH₃ | 4-OCH₃ | 2-Cl | H | Same as ex. 14 | H | H |
| Comp. 145 Ex. 45 | O | CH₃ | 4-OCH₃ | 2-F | H | Same as ex. 14 | H | H |
| Comp. 146 Ex. 46 | O | CH₃ | 4-Cl | 2-Cl | H | Same as ex. 33 | H | H |
| Comp. 147 Ex. 47 | O | CH₃ | 4-CH₃, 5-CH₃ | 2-Cl | H | Same as ex. 33 | H | H |
| Comp. 148 Ex. 48 | O | CH₃ | 5-CH₃ | 2-Cl | H | Same as ex. 33 | H | H |
| Comp. 149 Ex. 49 | O | CH₃ | H | 2-Cl | H | Same as ex. 14 | 3-OC₂H₅ | H |
| Comp. 150 Ex. 50 | O | CH₃ | H | 2-Cl | H | Same as ex. 14 | 1-OC₂H₅ | H |

TABLE 3-continued
Compounds of General formula
| Comp. No. Example No. | X | R₁ | R₂ | R₃ | R₄ | R₅ | R₆ | R₇ |
|---|---|---|---|---|---|---|---|---|
| Comp. 151 Ex. 51 | O | CH₃ | H | 2-Cl | H | 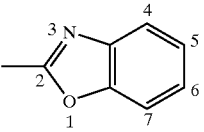 | — | — |
| Comp. 152 Ex. 52 | O | CH₃ | H | 2-Cl | H | 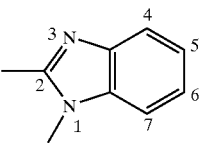 | — | — |
| Comp. 153 Ex. 53 | O | CH₃ | H | 2-Cl | H | 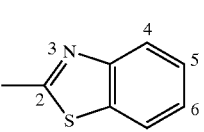 | — | — |
| Comp. 154 Ex. 54 | O | CH₃ | H | 2-Cl | H | 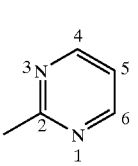 | — | — |
| Comp. 155 Ex. 55 | O | CH₃ | H | 2-Cl | H | 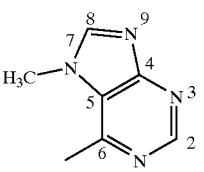 | — | — |
| Comp. 156 Ex. 56 | O | CH₃ | H | 2-Cl | H | 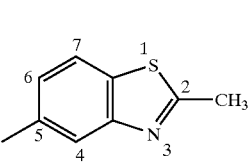 | — | — |
| Comp. 157 Ex. 57 | O | CH₃ | H | 2-Cl | H | 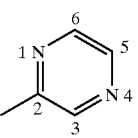 | — | — |
| Comp. 158 Ex. 58 | O | CH₃ | H | 2-Cl | H | 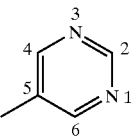 | — | — |
| Comp. 159 Ex. 59 | O | CH₃ | H | 2-Cl | H | 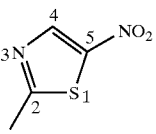 | — | — |

TABLE 3-continued

Compounds of General formula

| Comp. No. Example No. | X | R₁ | R₂ | R₃ | R₄ | R₅ | R₆ | R₇ |
|---|---|---|---|---|---|---|---|---|
| Comp. 160 ex. 60 | O | CH₃ | H | 2-Cl | H | ![triazole with NO2 and CH3] | — | — |

The numbering in Table 2 refers to the numbering in the formula below, $R_6$ and $R_7$ being defined as for general formula I:

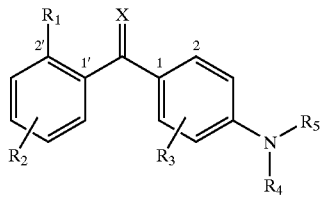

General Procedure 1

Coupling of compounds of the general formula II with compounds of the general formula III to give compounds of the general formula I, or a protected derivative thereof.

In a screw cap vessel an amine (1.0 eq.) with the general formula III was dissolved in 1,4-dioxane or toluene, and a halogenide (1.0–1.1 eq.), with the general formula II was added. The vessel was flushed with argon, the base ($Cs_2CO_3$ or NaOt-Bu, 1.4 eq.), $Pd_2(dba)_3$ (0.02 eq.), and BINAP (0.04 eq.) were added, the vessel was again flushed with argon and closed. The resulting suspension was first shaken vigorously at room temperature for 5 min and then at 100° C.–110° C. for 4–20 h or until the halogenide II had disappeared as seen on TLC. The reaction mixture was allowed to cool to room temperature. The reaction mixture was poured into a mixture of EtOAc and water. The organic phase was separated, and the water phase was extracted with EtOAc three times. The combined organic phases were washed with water and saturated aqueous NaCl dried ($MgSO_4$), filtered and concentrated in vacuo. The residue was purified either by chromatography and/or crystallisation to afford the coupled product with the general formula I, or a protected derivative thereof.

General Procedure 2

Coupling of compounds of the general formula II with compounds of the general formula III to give compounds of the general formula I, or a protected derivative thereof.

An amine of the general formula (III) (1 eq.) was dissolved in DMSO (0.1–0.2M), and a heteroarylchloride or heteroarylfluoride (1 eq.) of the general formula (II) was added. Potassium t-butoxide, 2 eq., or 3 eq. if compound II was provided as the hydrochloride, was dissolved in DMSO (0.2–0.4M), and the solution was added dropwise to the reaction mixture. The reaction was stirred under an argon atmosphere at 120–150° C. for 12–24 h. The reaction mixture was poured into water and extracted with EtOAc three times. The combined organic phases were washed with saturated aq. NaCl, dried ($MgSO_4$), filtered and concentrated in vacuo, and the crude product was purified by flash chromatography to afford the coupled product with the general formula I, or a protected derivative thereof.

General Procedure (3)

Coupling of compounds of the general formula VI with compounds of the general formula V to give compounds of the general formula IV, or a protected derivative thereof.

The bromide (80 mmol) with the general formula VI was dissolved in dry THF (65 mL) and cooled with stirring to −78° C. under an atmosphere of argon. n-Butyllithium (80 mmol, 1.6 M solution in hexane) was then added dropwise, keeping the internal temperature below −65° C. and stirring the resulting mixture for further 15 min. A THF solution of $ZnCl_2$ (100 mmol, 1.0 M) was added dropwise and the reaction mixture was allowed to warm to room temperature. After 2 h the reaction mixture was cooled to 0° C., and tetrakis(triphenylphosphine)palladium(0) (4.0 mmol) was added followed by the dropwise addition of the acid chloride (84 mmol), with the general formula V, in THF. The reaction mixture was allowed to warm to 20° C. and stirred for ca 16 h. The resulting yellow solution, was filtered and the filtrate poured into a mixture of EtOAc/water 1:1, shaken and separated. The aqueous phase was extracted with two more portions of EtOAc. The organic phases were combined, dried ($MgSO_4$), filtered, and concentrated in vacuo to afford the crude product. Further purification was done by flash chromatography and/or crystallisation to give the title compound IV, or a protected derivative thereof.

General Procedure (4)

Reduction of compounds of the general formula IV with stannous chloride dihydrate to give compounds of the general formula III, or a protected derivative thereof.

A mixture of a compound with the general formula IV (5 mmol) and stannous chloride dihydrate (5.64 g, 25 mmol) in absolute ethanol (50 mL) was heated to 70° C. under argon. After 1 hour, or until the starting material had disappeared as seen on TLC, the solution was allowed to cool to room temperature and then poured into ice/water. The pH was made alkaline by the addition of saturated sodium hydroxide (50 mL) before being extracted with ethyl acetate (3×100 mL). The organic phase was dried ($MgSO_4$), filtered and evaporated to afford the crude product. The crude product was further purified either by crystallisation or flash chromatography to yield the title compound or a protected derivative thereof.

General Procedure (5)

Oxidation of compounds of the general formula I with mCPBA to give the corresponding N-oxides A compound of the general formula I (1 eq.) was dissolved in $CH_2Cl_2$ and mCPBA (1.2 eq.) was added, and the reaction mixture was stirred at room temperature for 1–3 h. $Na_2S_2O_5$ (1.5 eq.) was added, and the suspension was stirred and filtered. $K_2CO_3$ (3 eq.) was added to the filtrate and stirred for 0.5–1 h. $MgSO_4$ was added, the suspension was filtered, and the filtrate was concentrated in vacuo. Purification by flash chromatography and/or by crystallisation.

PREPARTATION 1

2-Chloro-4-nitro-2'-methylbenzophenone, (Compound 1)

General Procedure: 3

Starting compound VI: 2-Bromotoluene
Starting compound V: 2-Chloro-4-nitro-benzoyl chloride
Purification: Chromatography using EtOAc/pentane 1:9 as eluant
$^{13}C$ NMR ($CDCl_3$): δ 195.1, 148.9, 145.5, 140.6, 135.0, 133.1, 132.7, 132.4, 131.9, 130.0, 125.9, 125.4, 121.9, 21.5.

PREPARATION 2

4-Amino-2-chloro-2'-methylbenzophenone, (Compound 2)

General Procedure: 4

Starting compound IV: 2-Chloro-4-nitro-2'-methylbenzophenone (Compound 1)
Purification: Chromatography using EtOAc/pentane 1:9 followed by 1:4 as eluant
$^{13}C$ NMR ($CDCl_3$): δ 196.7, 150.5, 139.5, 137.6, 135.1, 133.9, 131.2, 130.7, 129.5, 127.5, 125.3, 116.0, 112.2, 20.3.

PREPARATION 3

2-Chloro-4'-methoxy-2'-methyl-4-nitrobenzophenone (Compound 3)

General Procedure: 3

Starting compound VI: 2-Bromo-5-methoxytoluene
Starting compound V: 2-Chloro-4-nitro-benzoyl chloride
Purification: Crystallization from a MeOH/cyclohexane 10:1
$^{13}C$ NMR ($CDCl_3$): δ 193.3, 163.3, 148.6, 146.3, 144.3, 135.5, 132.4, 129.6, 127.5, 125.3, 121.9, 118.1, 110.9, 55.5, 22.4.

PREPARATION 4

4-Amino-2-chloro-4'-methoxy-2'-methylbenzophenone (Compound 4)

General Procedure: 4

Starting compound IV: 2-Chloro-4'-methoxy-2'-methyl-4-nitrobenzophenone (compound 3)
Purification: Filtered through a short column of silica gel
$^{13}C$ NMR ($CDCl_3$): δ 195.7, 161.7, 149.6, 141.6, 134.2, 133.3, 132.8, 131.4, 129.1, 117.0, 115.8, 112.4, 110.3, 55.3, 21.3.

PREPARATION 5

2,4'-Dichloro-2'-methyl-4-nitrobenzophenone (Compound 5)

General Procedure: 3

Starting compound VI: 2-Bromo-5-chlorotoluene
Starting compound V: 2-Chloro-4-nitro-benzoyl chloride
Purification: Chromatography using EtOAc/pentane 1:15 followed by 1:10 as eluant
$^{13}C$ NMR ($CDCl_3$): δ 194.1, 149.0, 145.0, 142.6, 139.4, 133.5, 133.1, 132.7, 132.5, 130.1, 126.1, 125.5, 122.0, 21.4.

PREPARATION 6

4-Amino-2,4'-dichloro-2'-methylbenzophenone (Compound 6)

General Procedure: 4

Starting compound IV: 2,4'-Dichloro-2'-methyl-4-nitrobenzophenone (compound 5)
$^{13}C$ NMR ($CDCl_3$): δ 195.4, 150.5, 139.8, 137.9, 136.5, 135.1, 133.7, 131.2, 130.9, 127.5, 125.6, 115.9, 112.3, 20.2.

PREPARATION 7

2-Chloro-4'-fluoro-2'-methyl-4-nitrobenzophenone (Compound 7)

General Procedure: 3

Starting compound VI: 2-Bromo-5-fluorotoluene
Starting compound V: 2-Chloro-4-nitro-benzoyl chloride
Purification: Chromatography using EtOAc/pentane 1:20 as eluant
$^{13}C$ NMR ($CDCl_3$): δ 193.7, 165.1, 148.9, 145.3, 144.6, 134.7, 132.6, 131.4, 129.9, 125.5, 122.0, 119.5, 113.0, 21.8.

PREPARATION 8

4-Amino-2-chloro-4'-fluoro-2'-methylbenzophenone (Compound 8)

General Procedure: 4

Starting compound IV: 2-Chloro-4'-fluoro-2'-methyl-4-nitrobenzophenone (compound 7)
Purification: Filtered through a short column of silica gel
$^{13}C$ NMR ($CDCl_3$): δ 195.4, 163.9, 150.3, 141.5, 135.5, 134.9, 133.5, 132.2, 128.0, 118.1, 115.9, 112.4, 112.3, 20.6.

PREPARATION 9

2-Fluoro-4-nitro-2'-methylbenzophenone (Compound 9)

General Procedure: 3

Starting compound VI: 2-Bromotoluene
Starting compound V: 2-Fluoro-4-nitro-benzoyl chloride
Purification: Crystallization from a mixture of MeOH/cyclohexane 6:1
$^{13}C$ NMR ($CDCl_3$): δ 193.1, 159.9, 150.3, 139.3, 136.4, 133.8, 132.6, 132.1, 131.7, 130.8, 125.8, 119.4, 112.4, 21.0.

PREPARATION 10

4-Amino-2-fluoro-2'-methylbenzophenone (Compound 10)

General Procedure: 4

Starting compound IV: 2-Fluoro-4-nitro-2'-methylbenzophenone (compound 9)
Purification: Filtered through a short column of silica gel
$^{13}C$ NMR ($CDCl_3$): δ 194.3, 163.8, 153.0, 140.7, 136.1, 134.0, 130.8, 129.9, 127.9, 125.3, 116.8, 110.1, 101.3, 19.8.

PREPARATION 11

2-Chloro-2',5'-dimethyl-4-nitrobenzophenone (Compound 11)

General Procedure: 3

Starting compound VI: 2-Bromo-1,4-dimethylbenzene
Starting compound V: 2-Chloro-4-nitro-benzoyl chloride
Purification: Filtered through a short column of silica gel
$^{13}$C NMR (CDCl$_3$): δ 195.3, 148.9, 145.6, 137.4, 135.5, 135.0, 133.9, 132.8, 132.3, 132.2, 130.0, 125.5, 121.9, 21.1, 20.8.

PREPARATION 12

4-Amino-2-chloro-2',5'-dimethylbenzophenone (Compound 12)

General Procedure: 4

Starting compound IV: 2-Chloro-2',5'-dimethyl-4-nitrobenzophenone (compound 11)
Purification: Filtered through a short column of silica gel
$^{13}$C NMR (CDCl$_3$): δ 196.8, 150.2, 139.3, 135.1, 134.9, 134.5, 133.8, 131.4, 131.1, 130.0, 128.0, 116.0, 112.2, 20.8, 19.9.

PREPARATION 13

2,3'-Dichloro-2'-methyl-4-nitrobenzophenone (Compound 13)

General Procedure: 3

Starting compound VI: 2-Bromo-3-chlorotoluene
Starting compound V: 2-Chloro-4-nitro-benzoyl chloride
Purification: Crystallization from a mixture of MeOH/cyclohexane 9:1
$^{13}$C NMR (CDCl$_3$): δ 194.6, 149.2, 144.5, 138.2, 137.3, 137.0, 133.5, 133.2, 130.7, 129.0, 126.5, 125.7, 122.0, 17.3.

PREPARATION 14

4-Amino-2,3'-dichloro-2'-methylbenzophenone (Compound 14)

General Procedure: 4

Starting compound IV: 2,3'-Dichloro-2'-methyl-4-nitrobenzophenone (compound 13)
Purification: Filtered through a short column of silica gel
$^{13}$C NMR (CDCl$_3$): δ 195.3, 150.9, 142.4, 135.8, 135.8, 134.8, 134.6, 131.0, 126.8, 126.7, 126.4, 116.2, 112.2, 17.1.

PREPARATION 15

2-Fluoro-4'-methoxy-2'-methyl-4-nitrobenzophenone (Compound 15)

General Procedure: 3

Starting compound VI: 2-Bromo-5-methoxytoluene
Starting compound V: 2-Fluoro-4-nitro-benzoyl chloride
Purification: Recrystallization from a mixture of MeOH/cyclohexane/CH$_2$Cl$_2$
$^{13}$C NMR (CDCl$_3$): δ 191.3, 163.1, 159.3, 143.6, 135.0, 134.8, 131.2, 128.5, 119.4, 117.8, 112.2, 110.8, 55.5, 22.1.

PREPARATION 16

4-Amino-2-fluoro-4'-methoxy-2'-methylbenzophenone (Compound 16)

General Procedure: 4

Starting compound IV: 2-Fluoro-4'-methoxy-2'-methyl-4-nitrobenzophenone (compound
Purification: Filtered through a short column of silica gel
$^{13}$C NMR (CDCl$_3$): δ 193.4, 163.1, 161.2, 152.2, 140.1, 133.7, 132.6, 131.7, 117.8, 116.6, 110.3, 110.1, 101.3, 55.3, 20.7.

PREPARATION 17

2-Chloro-4-nitro-2',4',5'-trimethylbenzophenone (Compound 17

General Procedure: 3

Starting compound VI: 5-Bromo-1,2,4-trimethylbenzene
Starting compound V: 2-Chloro-4-nitro-benzoyl chloride
Purification: Recrystallisation from EtOAc
EO 01720-000 (CDCL3)
$^{13}$C NMR (CDCl$_3$): δ 194.8, 148.7, 146.1, 143.0, 138.3, 134.1, 134.0, 133.4, 132.6, 132.5, 129.8, 125.4, 121.9, 21.2, 19.9, 19.2.

PREPARATION 18

4-Amino-2-chloro-2',4',5'-trimethylbenzophenone (Compound 18)

General Procedure: 4

Starting compound IV: 2-Chloro-4-nitro-2',4',5'-trimethylbenzophenone (compound 17)
Purification: Filtered through a short column of silica gel
$^{13}$C NMR (CDCl$_3$): δ 196.6, 149.9, 140.0, 136.6, 135.5, 134.7, 133.4, 132.7, 131.4, 128.5, 115.9, 112.2, 20.0, 19.7, 19.1.

PREPARATION 19

4'-n-Butyl-2-chloro-2'-methyl-4-nitrobenzophenone (Compound 19)

General Procedure: 3

Starting compound VI: 4-n-Butyl-2-methyliodobenzene
Starting compound V: 2-Chloro-4-nitro-benzoyl chloride
Purification: Chromatography, eluent EtOAc:Petroleumethet 1:15
$^{13}$C NMR (CDCl$_3$): δ 194.6, 149.2, 148.7, 146.0, 141.1, 132.7, 132.7, 132.6, 132.3, 129.8, 125.9, 125.3, 121.8, 35.7, 33.1, 22.4, 21.8, 13.9.

PREPARATION 20

4-Amino-4'-n-butyl-2-chloro-2'-methylbenzophenone (Compound 20)

General Procedure: 4

Starting compound IV: 4'-n-Butyl-2-chloro-2'-methyl-4-nitrobenzophenone (compound 19)
Purification: Filtered through a short column of silica gel
$^{13}$C NMR (CDCl$_3$): δ 196.5, 150.0, 146.3, 138.3, 136.5, 134.7, 133.4, 131.5, 130.4, 128.4, 125.3, 115.9, 112.2, 35.6, 33.3, 22.4, 20.6, 13.9.

EXAMPLE 1

2-Chloro-2'-methyl-4-(4-pyridylamino) benzophenone (Compound 101),

General Procedure: 2

Starting compound II: 4-chloro-pyridine hydrochloride (0.30 g, 2.0 mmol)
Starting compound III: 4-Amino-2-chloro-2'-methylbenzophenone (compound 2) (0.49 g, 2.0 mmol)
Solvent: DMSO (15 mL)
Base: t-BuOK (0.67 g, 6.0 mmol) in DMSO (10 mL)
Reaction time: 22 h
Reaction temperature: 150° C.
Purification: Chromatography using EtOAc:MeOH 15:1
Product: Compound 101, 0.20 g oil
$^1$H NMR (CDCl$_3$): δ 8.39(d,1H), 7.43(d,1H), 7.40–7.20 (m,5H), 7.08(dd,1H), 6.97(d,3H), 2.50(s,3H)

EXAMPLE 2

2-Chloro-2'-methyl-4-(2-pyridylamino) benzophenone (Compound 102),

General Procedure: 2

Starting compound II: 2-chloro-pyridine (0.19 mL, 2.0 mmol)
Starting compound III: 4-Amino-2-chloro-2'-methylbenzophenone (compound 2) (0.49 g, 2.0 mmol)
Solvent: DMSO (15 mL)
Base: t-BuOK (0.45 g, 4.0 mmol) in DMSO (10 mL)
Reaction time: 22 h
Reaction temperature: 150° C.
Purification: Chromatography using EtOAc:petroleum ether 1:5
Product: Compound 102, 0.21 g oil.
$^1$H NMR (CDCl$_3$): δ 8.28(d,1H), 7.65(d,1H), 7.58(t,1H), 7.41(d,1H), 7.40–7.25(m,4H), 7.19(t,1H), 6.95(s,1H), 6.86 (m,2H), 2.47(s,3H).

EXAMPLE 3

2-Chloro-2'-methyl-4-(5-nitro-2-pyridylamino) benzophenone (Compound 103),

General Procedure: 2

Starting compound II: 2-chloro-5-nitro-pyridine (0.32 g, 2.0 mmol)
Starting compound III: 4-Amino-2-chloro-2'-methylbenzophenone (compound 2) (0.49 g, 2.0 mmol)
Solvent: DMSO (10 mL)
Base: t-BuOK (0.45 g, 4.0 mmol) in DMSO (20 mL)
Reaction time: 18 h
Reaction temperature: 150° C.
Purification: Chromatography using EtOAc:petroleum ether 2:7–1:3
Product: Compound 103, 0.09 g crystalline compound
$^{13}$C NMR (acetone d-6): δ 196.7, 159.4, 146.2, 144.2, 139.2, 139.0, 138.8, 133.8, 133.6, 133.5, 132.4, 132.4, 132.3, 131.0, 126.5, 121.0, 118.3, 112.1, 20.8.

EXAMPLE 4

4-(6-Amino-5-nitro-2-pyridylamino)-2-chloro-2'-methylbenzophenone (Compound 104), General Procedure: 2

Starting compound II: 2-amino-6-chloro-3-nitro-pyridine (0.69 g, 4.0 mmol)
Starting compound III: 4-Amino-2-chloro-2'-methylbenzophenone (compound 2) (0.98 g, 4.0 mmol)
Solvent: DMSO (15 mL)
Base: t-BuOK (0.90 g, 8.0 mmol) in DMSO (25 mL)
Reaction time: 48 h
Reaction temperature: 150° C.
Purification: Chromatography using CH$_2$Cl$_2$: EtOAc 50:1–30:1
Product: Compound 104, 0.58 g crystalline compound
$^{13}$C NMR (DMSO): δ 195.9, 157.7, 154.7, 143.5, 138.0, 137.4, 135.7, 131.9, 131.8, 131.5, 131.4, 129.9, 125.8, 119.9, 119.5, 117.5, 103.2, 20.2.

EXAMPLE 5

6-Chloro-2-(3-chloro-4-(2-methylbenzoyl) phenylamino)isonicotinic Acid (Compound 105), General Procedure: 2

Starting compound II: 2,6-dichloro-4-cyano-pyridine (0.70 g, 4.0 mmol)
Starting compound III: 4-Amino-2-chloro-2'-methylbenzophenone (compound 2) (0.98 g, 4.0 mmol)
Solvent: DMSO (15 mL)
Base: t-BuOK (0.90 g, 8.0 mmol) in DMSO (25 mL)
Reaction time: 48 h
Reaction temperature: 150° C.
Purification: Chromatography using EtOAc:MeOH 5:1
Product: Compound 105, 0.52 g oil, the cyano substituent has been hydrolysed during reaction or work up.
$^{13}$C NMR (DMSO): δ 195.7, 166.6, 154.8, 150.5, 147.2, 145.0, 138.4, 137.0, 132.3, 132.1, 131.2, 131.1, 129.5, 129.4, 125.7, 118.0, 115.6, 114.8, 111.3, 20.0.

EXAMPLE 6

4-(6-Carbonitrile-2-pyridylamino)-2-chloro-2'-methylbenzophenone (Compound 106), General Procedure: 2

Starting compound II: 2-chloro-3-cyano-pyridine (0.28 g, 2.0 mmol)
Starting compound III: 4-Amino-2-chloro-2'-methylbenzophenone (compound 2) (0.49 g, 2.0 mmol)
Solvent: DMSO (10 mL)
Base: t-BuOK (0.45 g, 4.0 mmol) in DMSO (20 mL)
Reaction time: 18 h
Reaction temperature: 150° C.
Purification: Chromatography using EtOAc:petroleum ether 1:1–1:0
Product: Compound 106, 0.07 g crystalline compound
$^{13}$C NMR (CDCl$_3$): δ 195.9, 155.5, 144.3, 142.9, 142.1, 140.3, 140.0, 136.0, 133.2, 132.6, 132.1, 131.8, 131.1, 128.8, 125.7, 125.3, 115.7, 105.7, 102.4, 21.3.

EXAMPLE 7

2-Chloro-2'-methyl-4-(3-pyridylamino) benzophenone (Compound 107),

General Procedure: 1

Starting compound II: 3-chloro-pyridine (1.18 mL, 12.0 mmol)

Starting compound III: 4-Amino-2-chloro-2'-methylbenzophenone (compound 2) (2.95 g, 12.0 mmol)

Solvent: Toluene (60 mL)

Base: t-BuONa

Reaction time: 45 h

Reaction temperature: 110° C.

Purification: Chromatography using $CH_2Cl_2$: acetone 4:1

Product: Compound 107, 2.05 g crystalline compound $^{13}C$ NMR ($CDCl_3$): δ 196.5, 146.8, 144.4, 142.7, 138.7, 138.1, 137.3, 134.9, 133.3, 131.4, 131.1, 130.4, 129.9, 127.1, 125.4, 124.0, 117.0, 113.4, 20.5.

EXAMPLE 8

2-Chloro-4-(5,6-diamino-2-pyridylamino)-2'-methylbenzophenone (Compound 108), Compound 104 (0.38 g, 1.0 mmol) was dissolved in EtOH (10 mL) and DMF (10 mL). $SnCl_2$ *$H_2O$ (1.12 g, 5.0 mmol) was added and the solution was stirred at 90° C. for 20 h. The reaction mixture was poured into ice water (100 mL), 2 N NaOH (50 mL) was added, and the water phase was extracted with EtOAc (50 mL) and $Et_2O$ (2×50 mL). The combined organic phases were washed with saturated aqueous NaCl (50 mL), dried ($Na_2SO_4$), filtered and concentrated in vacuo. The residue was purified by flash chromatography EtOAc:petroleum ether 2:1–1:0.

Product: Compound 108, 0.05 g oil $^{13}C$ NMR ($CDCl_3$): δ 196.7, 148.9, 146.2, 145.6, 139.2, 137.9, 134.6, 133.1, 131.2, 130.8, 129.7, 129.2, 126.7, 125.4, 122.5, 117.4, 114.0, 102.1, 20.4

EXAMPLE 9

2-Chloro-2'-methyl-4-(3-nitro-2-pyridylamino) benzophenone (Compound 109),

2-Chloro-3-nitro-pyridine (0.32 g, 2.0 mmol) and 4-amino-2-chloro-2'-methylbenzophenone (compound 2) (0.49 g, 2.0 mmol) was mixed thoroughly. The reaction mixture was warmed at 100° C. for 0.5 h and then at 160° C. for 0.5 h. The reaction mixture was cooled to room temperature, and dissolved in saturated aqueous $NaHCO_3$ (10 mL) and EtOAc (30 mL). The phases were separated, and the organic phase was washed with saturated aqueous $NaHCO_3$ (10 mL), dried ($MgSO_4$), filtered and concentrated in vacuo.

Purification by flash chromatography using EtOAc: petroleum ether 1:7.

Product: Compound 109, 0.26 g crystalline compound which was recrystallised from $Et_2O$ $^{13}C$ NMR ($CDCl_3$): δ 196.6, 154.8, 149.2, 141.4, 138.9, 137.9, 135.6, 134.2, 133.4, 131.6, 131.6, 131.5, 130.6, 129.4, 125.5, 122.5, 119.0, 115.3, 20.9.

EXAMPLE 10

4-(3-Amino-2-pyridylamino)-2-chloro-2'-methylbenzophenone (Compound 110),

Compound 109 (0.15 g, 0.4 mmol) was suspended in EtOH (10 mL) and $SnCl_2$ *$H_2O$ (0.46 g, 2.0 mmol) was added. The reaction mixture was stirred at 70° C. for 1 h, after which it was poured into ice water (50 mL). 2N NaOH (50 mL) was added and the water phase was extracted with EtOAc (3×20 mL). The combined organic phases were dried (MgSO4), filtered and concentrated in vacuo. Purification by flash chromatography using EtOAc:petroleum ether 2:3.

Product: Compound 110, 0.12 g oil.

$^{13}C$ NMR ($CDCl_3$): δ 196.9, 145.3, 143.9, 139.2, 138.9, 138.1, 134.2, 132.7, 131.7, 131.3, 131.0, 130.3, 130.0, 125.4, 124.6, 118.8, 118.5, 114.9, 20.5.

EXAMPLE 11

4-(5-Amino-2-pyridylamino)-2-chloro-2'-methylbenzophenone (Compound 111),

Compound 103 (0.07 g, 0.19 mmol) was suspended in EtOH (5 mL) and $SnCl_2$ *$H_2O$ (0.21 g, 1.0 mmol) was added. The reaction mixture was stirred at 70° C. for 3 h and the reaction mixture was worked up as described for Compound 110. Purification by flash chromatography using EtOAc:petroleum ether 3:2.

Product: Compound 111, 0.038 g oil $^{13}C$ NMR ($CDCl_3$): δ 196.7, 146.3, 146.0, 139.1, 137.9, 137.6, 135.1, 134.6, 133.1, 131.3, 130.9, 129.8, 129.6, 125.5, 125.4, 117.3, 113.9, 112.7, 20.5.

EXAMPLE 12

2-Chloro-2'-methyl-4((2-pyridyl-N-oxide)amino) benzophenone (Compound 112)

General Procedure: 5

Starting compound I: Compound 102 (0.16 g, 0.5 mmol)

Reaction time: 1 h

Purification by chromatography using EtOAc:MeOH 8:1

Product: Compound 112, 0.098 g crystalline compound which could be recrystallised from MeOH $^{13}C$ NMR (DMSO): δ 195.8, 146.0, 142.8, 137.7, 137.5, 132.2, 132.0, 131.8, 131.6, 131.4, 130.0, 127.0, 125.8, 121.0, 117.7, 116.1, 109.8, 20.2.

EXAMPLE 13

2-Chloro-2'-methyl-4((3-pyridyl-N-oxide)amino) benzophenone (Compound 113)

General Procedure: 5

Starting compound I: Compound 107 (0.18 g, 0.54 mmol)

Reaction time: 2 h

Purification by chromatography using EtOAc:MeOH 7:1

Product: Compound 113, 0.12 g crystalline compound $^{13}C$ NMR ($CD_3OD$): δ 198.5, 146.6, 143.7, 139.7, 139.4, 135.4, 134.0, 133.2, 133.0, 132.7, 132.6, 131.2, 130.4, 128.1, 126.8, 120.0, 119.6, 116.5, 20.8.

EXAMPLE 14

2-Chloro-4-(4-isoquinolylamino)-2'-methylbenzophenone (Compound 114),

General Procedure: 1

Starting compound II: 4-bromo-isoquinoline (0.42 g, 2.0 mmol)
Starting compound III: 4-Amino-2-chloro-2'-methylbenzophenone (compound 2) (0.49, 2.0 mmol)
Solvent: 1,4-dioxane (6 mL)
Base: t-BuONa
Reaction time: 18 h
Reaction temperature: 100° C.
Purification: Chromatography using $CH_2Cl_2$: acetone 10:1
Product: Compound 114, 0.64 g amorphous compound.
$^{13}$C NMR ($CDCl_3$): δ 196.6, 150.1, 149.3, 139.0, 138.6, 137.9, 135.1, 133.5, 132.1, 131.3, 131.1, 130.9, 130.8, 129.7, 129.3, 129.3, 128.2, 127.9, 125.4, 121.6, 116.3, 112.6, 20.5.

EXAMPLE 15 t-Butyl 5-(3-chloro-4-(2-methylbenzoyl)phenylamino)nicotinoate (Compound 115,)

5-Bromonicotinic acid (4.7 g, 23 mmol) was added to 7 mL condensed isobutylene in $CH_2Cl_2$ (15 mL), and afterwards conc. $H_2SO_4$ (0.75 mL) was added. The reaction mixture was stirred in a screw cap vessel for 24 h at room temperature, after which it was poured into saturated aqueous $NaHCO_3$ (100 mL). The aqueous phase was extracted with EtOAc (100 mL), the organic phase was washed with $NaHCO_3$, dried ($MgSO_4$), filtered and concentrated. The crude product was purified by chromatography using the eluent EtOAc:petroleum ether 1:10.
Product: t-butyl 5-bromonicotinoate, crystalline compound.
$^{13}$C NMR ($CDCl_3$): δ 163.06, 154.02, 148.85, 139. 38, 129.10, 120.48, 82.82, 28.12

General Procedure: 1

Starting compound II: t-Butyl 5-bromonicotinoate, (0.12 g, 0.45 mmol)
Starting compound III: 4-Amino-2-chloro-2'-methylbenzophenone (compound 2) (0.13 g, 0.53 mmol)
Solvent: toluene (3 mL)
Base: t-BuONa
Reaction time: 12 h
Reaction temperature: 100° C.
Purification: Chromatography using EtOAc:petroleum ether 1:2
Product: Compound 115, 0.035 g oil
$^{13}$C NMR ($CDCl_3$): δ 196.7, 164.1, 146.1, 145.1, 144.8, 138.5, 138.2, 137.4, 134.8, 133.2, 131.5, 131.3, 131.0, 130.1, 128.4, 126.9, 125.5, 117.7, 113.7, 82.5, 28.1, 20.6.

EXAMPLE 16

2-Chloro-2'-methyl-4-(4-methyl-3-pyridylamino)benzophenone (Compound 116),

General Procedure: 1

Starting compound II: 3-bromo-4-methyl pyridine (0.172 g, 1.0 mmol)
Starting compound III: 4-Amino-2-chloro-2'-methylbenzophenone (compound 2)(0.25 g, 1.0 mmol)
Solvent: 1,4-dioxane (5 mL)
Base: t-BuONa
Reaction time: 18 h
Reaction temperature: 110° C.
Purification: Chromatography using EtOAc:petroleum ether 1:3–1:1
Product: Compound 116, 0.08 g oil
$^{13}$C NMR ($CDCl_3$): δ 196.5, 148.5, 146.5, 146.1, 142.1, 139.0, 138.0, 135.4, 135.1, 133.5, 131.3, 131.0, 129.8, 129.3, 125.9, 125.4, 116.0, 112.3, 20.5, 17.5.

EXAMPLE 17

2-Chloro-2'-methyl-4-(6-methyl-3-pyridylamino)benzophenone (Compound 117),

General Procedure: 1

Starting compound II: 5-bromo-2-methyl pyridine (0.172 g, 1.0 mmol)
Starting compound III: 4-Amino-2-chloro-2'-methylbenzophenone (compound 2) (0.25 g, 1.0 mmol)
Solvent: 1,4-dioxane (5 mL)
Base: t-BuONa
Reaction time: 18 h
Reaction temperature: 110° C.
Purification: Chromatography using EtOAc:petroleum ether 1:4–1:2
Product: Compound 117, 0.15 g oil
$^1$H NMR ($CDCl_3$): δ 8.37(d,1H), 7.45(dd,1H), 7.4–7.15 (m,6H), 6.93(d,1H), 6.78(dd,1H), 6.29(s,1H), 2.54(s,3H), 2.44(s,3H).

EXAMPLE 18

4-(5-Bromo-3-pyridylamino)-2-chloro-2'-methylbenzopfhenone (Compound 118),

General Procedure: 1

Starting compound II: 3,5-dibromo-pyridine (0.237 g, 1.0 mmol)
Starting compound III: 4-Amino-2-chloro-2'-methylbenzophenone (compound 2) (0.25 g, 1.0 mmol)
Solvent: 1,4-dioxane (5 mL)
Base: t-BuONa
Reaction time: 5 h
Reaction temperature: 110° C.
Purification: Chromatography using acetone:$CH_2Cl_2$ 1:10
Product: Compound 118, 0.05 g oil
$^{13}$C NMR ($CDCl_3$): δ 196.6, 145.4, 144.7, 139.9, 138.6, 138.4, 138.3, 134.8, 133.0, 131.6, 131.6, 131.4, 130.2, 128.3, 125.5, 120.8, 118.1, 114.3, 20.7.

EXAMPLE 19

4-(5-Carbonitrile-3-pyridylamino)-2-chloro-2'-methylbenzophenone (Compound 119), General Procedure: 1

Starting compound II: 5-bromonicotinonitrile (0.22 g, 1.2 mmol)
Starting compound III: 4-Amino-2-chloro-2'-methylbenzophenone (compound 2) (0.25 g, 1.0 mmol)
Solvent: Toluene (5 mL)
Base: $Cs_2CO_3$
Reaction time: 18 h
Reaction temperature: 100° C.
Purification: Chromatography using EtOAc:petroleum ether 1:2
Product: Compound 119, 0.11 g oil
$^{13}$C NMR (DMSO): δ 195.6, 145.8, 144.5, 144.5, 138.4, 138.1, 137.1, 133.0, 131.3, 131.3, 129.8, 129.5, 126.6, 125.8, 117.3, 116.9, 114.2, 109.3, 20.1.

EXAMPLE 20

4-(3-Bromo-2-pyridylamino)-2-chloro-2'-methylbenzophenone (Compound 120),

General Procedure: 1

Starting compound II: 3-bromo-2-chloro-pyridine (0.23 g, 1.2 mmol)

Starting compound III: 4-Amino-2-chloro-2'-methylbenzophenone (compound 2) (0.25 g, 1.0 mmol)

Solvent: 1,4-dioxane (5 mL)

Base: t-BuONa

Reaction time: 18 h

Reaction temperature: 100° C.

Purification: reversed phase HPLC, (0.1% TFA in $H_2O$):(0.1% TFA in 90% CH3CN+10% $H_2O$) 1:1–0:1

Product: Compound 120

$^{13}$C NMR (CDCl$_3$): δ 196.7, 150.8, 146.5, 143.3, 140.6, 138.5, 133.8, 132.1, 131.5, 131.3, 130.3, 125.4, 119.9, 117.2, 116.4, 107.0, 20.7.

EXAMPLE 21

2-Chloro-2'-methyl-4-(8-quinolylamino)benzophenone (Compound 121),

General Procedure: 1

Starting compound II: 8-bromo-quinoline (0.16 mL, 1.25 mmol)

Starting compound III: 4-Amino-2-chloro-2'-methylbenzophenone (compound 2) (0.28 g, 1.14 mmol)

Solvent: 1,4-dioxane (5 mL)

Base: t-BuONa

Reaction time: 18 h

Reaction temperature: 100° C.

Purification: Flash chromatography using Et$_2$O:petroleum ether 1:3

Product: Compound 121, 0.28 g crystalline compound which was recrystallised from Et$_2$O $^{13}$C NMR (CDCl$_3$): δ 196.5, 147.9, 145.9, 139.0, 138.9, 138.1, 137.7, 136.4, 134.7, 133.1, 131.4, 131.0, 130.6, 129.9, 128.8, 127.0, 125.4, 121.9, 119.1, 118.7, 115.3, 110.7, 20.6.

EXAMPLE 22

2-Chloro-4-(6-ethoxy-3-pyridylamino)-2'-methylbenzophenone (Compound 122),

General Procedure: 1

Starting compound II: 5-bromo-2-ethoxy-pyridine (0.24 g, 1.2 mmol)

Starting compound III: 4-Amino-2-chloro-2'-methylbenzophenone (compound 2) (0.25 g, 1.0 mmol)

Solvent: 1,4-dioxane (5 mL)

Base: t-BuONa

Reaction time: 18 h

Reaction temperature: 100° C.

Purification: reversed phase HPLC

Product: Compound 122

$^1$H NMR (CDCl$_3$): δ 8.09(d,1H), 7.54(dd,1H), 7.40–7.20 (m,5H), 6.80(m,2H), 6.66(dd,1H), 4.35(q,2H), 2.43(s,3H), 1.42(t,3H).

EXAMPLE 23

4-(4-Bromo-1-isoquinolylamino)-2-chloro-2'-methylbenzophenone (Compound 123), General Procedure: 1

Starting compound II: 4-bromo-1-chloroisoquinoline (0.14 g, 0.5 mmol)

Starting compound III: 4-Amino-2-chloro-2'-methylbenzophenone (compound 2) (0.13 g, 0.56 mmol)

Solvent: 1,4-dioxane (3 mL)

Base: t-BuONa

Reaction time: 18 h

Reaction temperature: 100° C.

Purification: reversed phase HPLC

Product: Compound 123

$^1$H NMR (CDCl$_3$): δ 8.24(s,1H), 8.18(d,1H), 8.00(d,1H), 7.85(t,1H), 7.77(d,1H), 7.65(t,1H), 7.45–7.35(m,4H), 7.28 (d,1H), 7.20(t,1H), 2.52(s,3H).

EXAMPLE 24

2-Chloro-2'-methyl-4-(2-methyl-5-trifluoromethyl-3-pyridylamino)benzophenone (Compound 124), General Procedure: 1, without Pd$_2$(dba)$_3$ and BINAP Starting compound II: 3-Chloro-2-methyl-5-(trifluoromethyl)pyridine (0.20, 1.0 mmol)

Starting compound III: 4-Amino-2-chloro-2'-methylbenzophenone (compound 2) (0.25 g, 1.0 mmol)

Solvent: 1,4-dioxane (5 mL)

Base: t-BuONa

Catalyst: Pd(P(cyclohexyl)$_3$)$_2$Cl$_2$ (30 mg, 0.04 mmol)

Reaction time: 18 h

Reaction temperature: 110° C.

Purification: reversed phase HPLC

Product: Compound 124

$^{13}$C NMR (CDCl$_3$): δ 196.4, 152.6, 144.5, 138.8, 137.9, 137.5, 137.2, 134.8, 133.0, 132.9, 131.7, 130.4, 125.6, 123.8, 119.4, 115.4, 20.8, 19.5.

EXAMPLE 25

2-Chloro-2'-methyl-4-(3-quinolylamino)benzophenone (Compound 125),

General Procedure: 1

Starting compound II: 3-bromo-quinoline (0.23 g, 1.1 mmol)

Starting compound III: 4-Amino-2-chloro-2'-methylbenzophenone (compound 2)(0.25 g, 1.0 mmol)

Solvent: 1,4-dioxane (5 mL)

Base: t-BuONa

Reaction time: 18 h

Reaction temperature: 100° C.

Purification by flash chromatography using EtOAc:petroleum ether 2:3

Product: Compound 125, 0.23 g amorphous compound.

$^{13}$C NMR (CDCl$_3$): δ 196.5, 146.6, 146.1, 144.9, 138.7, 138.2, 135.0, 134.2, 133.3, 131.4, 131.2, 130.7, 130.0, 129.2, 128.4, 128.0, 127.5, 126.9, 125.5, 122.4, 117.2, 113.6, 20.6.

EXAMPLE 26

2-Chloro-4-(4-ethoxy-3-pyridylamino)-2'-methylbenzophenone (Compound 126),

General Procedure: 1

Starting compound II: 3-bromo-4-ethoxypyridine (0.22 g, 1.1 mmol)
Starting compound III: 4-Amino-2-chloro-2'-methylbenzophenone (compound 2) (0.25 g, 1.0 mmol)
Solvent: 1,4-dioxane (6 mL)
Base: t-BuONa
Reaction time: 7 h
Reaction temperature: 100° C.
Purification by flash chromatography using EtOAc:petroleum ether 1:3–1:0 followed by reversed phase HPLC.
Product: Compound 126, oil.
$^{13}$C NMR (CDCl$_3$): δ 196.3, 158.5, 142.6, 138.9, 137.5, 136.5, 134.3, 134.1, 132.5, 131.9, 131.8, 131.6, 130.7, 126.8, 125.7, 120.8, 116.8, 107.7, 66.9, 20.9, 14.2.

EXAMPLE 27

2-Chloro-4-(2-ethoxy-3-pyridylamino)-2'-methylbenzophenone (Compound 127),

General Procedure: 1

Starting compound II: 3-bromo-2-ethoxypyridine (0.22 g, 1.1 mmol)
Starting compound III: 4-Amino-2-chloro-2'-methylbenzophenone (compound 2) (0.25 g, 1.0 mmol)
Solvent: 1,4-dioxane (6 mL)
Base: t-BuONa
Reaction time: 3 h
Reaction temperature: 100° C.
Purification by flash chromatography using EtOAc:petroleum ether 1:5
Product: Compound 127, 0.20 g oil.
$^{13}$C NMR (CDCl$_3$): δ 196.4, 154.1, 145.9, 138.8, 138.7, 138.2, 134.8, 133.1, 131.4, 131.1, 130.5, 129.9, 125.4, 125.2, 122.8, 117.8, 116.6, 114.3, 62.2, 20.5, 14.7.

EXAMPLE 28

2-Chloro-4((4-isoquinolyl-N-oxide)amino)-2'-methylbenzophenone (Compound 128)

General Procedure: 5

Starting compound I: Compound 114 (0.37 g, 1.0 mmol)
Reaction time: 2 h
Purification by chromatography using EtOAc:MeOH 8:1
Product: Compound 128, 0.22 g crystalline compound
$^{13}$C NMR (DMSO): δ 195.5, 147.5, 138.3, 137.0, 136.0, 132.9, 131.2, 131.2, 130.9, 129.9, 129.7, 129.5, 127.9, 125.7, 125.3, 123.4, 122.1, 117.7, 114.6, 20.0.

EXAMPLE 29

2-Chloro-2'-methyl-4-(2-methyl-6-quinolylamino)benzophenone (Compound 129),

General Procedure: 1

Starting compound II: 6-bromoquinaldine (0.24 g, 1.1 mmol)
Starting compound III: 4-Amino-2-chloro-2'-methylbenzophenone (compound 2) (0.25 g, 1.0 mmol)
Solvent: 1,4-dioxane (6 mL)
Base: t-BuONa
Reaction time: 18 h
Reaction temperature: 100° C.
Purification by flash chromatography using EtOAc:petroleum ether 1:1
Product: Compound 129, 0.27 g oil.
$^{13}$C NMR (CDCl$_3$): δ 196.6, 157.7, 147.3, 144.9, 139.0, 138.0, 137.9, 135.2, 135.0, 133.4, 131.3, 131.0, 130.2, 129.9, 129.8, 127.3, 125.4, 124.6, 122.7, 117.1, 115.2, 113.5, 25.1, 20.5.

EXAMPLE 30

2-Chloro-4-(7-chloro-4-quinolylamino)-2'-methylbenzophenone (Compound 130), 4,7-Dichloroquinoline (0.20 g, 1.0 mmol) was dissolved in i-PrOH (10 mL) and 4-amino-2-chloro-2'-methylbenzophenone (compound 2) (0.27 g, 1.1 mmol) was added. The reaction mixture was stirred at reflux for 2 h, after which it was poured into saturated aqueous NaHCO$_3$ (30 mL). The water phase was extracted with EtOAc (3×30 mL), the combined organic phases were washed with brine, dried (MgSO$_4$), filtered and concentrated in vacuo. Purification by flash chromatography using EtOAc:petroleum ether 1:3–1:1.

Product: Compound 130, 0.28 g crystalline compound.
$^{13}$C NMR (DMSO): δ 195.67, 152.08, 149.58, 145.60, 145.01, 137.84, 137.39, 134.19, 132.34, 132.26, 131.50, 131.39, 129.82, 127.78, 125.76, 125.65, 124.51, 120.52, 119.25, 117.52, 105.38, 20.13.

EXAMPLE 31

2-Chloro-2'-methyl-4-(2-quinolylamino)benzophenone (Compound 131),

2-Chloroquinoline (0.16 g, 1.0 mmol) was dissolved in i-PrOH (10 mL) and 4-amino-2-chloro-2'-methylbenzophenone (compound 2) (0.27 g, 1.1 mmol) was added. The reaction mixture was stirred at reflux for 18 h, and the reaction mixture was worked up as described for the synthesis of Compound 130

Purification by flash chromatography using EtOAc:petroleum ether 1:4.

Product: Compound 131, 0.24 g oil
$^{13}$C NMR (CDCl$_3$): δ 196.9, 152.6, 147.1, 144.1, 138.6, 138.4, 138.1, 134.0, 132.4, 131.6, 131.4, 131.2, 130.2, 130.1, 127.4, 127.3, 125.5, 124.5, 124.1, 119.8, 116.1, 112.9, 20.7.

EXAMPLE 32

2-Chloro-2'-methyl-4-(4-quinolylamino)benzophenone (Compound 132),

4-Chloroquinoline (0.16 g, 1.0 mmol) was dissolved in I-PrOH (10 mL) and 4-amino-2-chloro-2'-methylbenzophenone (compound 2) (0.27 g, 1.1 mmol) was added. The reaction mixture was stirred at reflux for 18 h, after which it was poured into saturated aqueous NaHCO$_3$ (30 mL). The water phase was extracted with EtOAc (3×30 mL), the combined organic phases were washed with brine, dried (MgSO$_4$), filtered and concentrated in vacuo.

Purification by flash chromatography using EtOAc:petroleum ether 1:3–1:1.

Product: Compound 132, 0.16 g amorphous compound.
$^{13}$C NMR (CDCl$_3$): δ 196.58, 150.79, 149.37, 145.25, 144.37, 138.74, 137.98, 134.30, 133.22, 132.51, 131.67, 131.61, 130.45, 130.28, 129.84, 126.10, 125.54, 121.10, 120.75, 120.07, 117.54, 105.43, 20.80.

EXAMPLE 33

2-Chloro-2'-methyl-4-(1-methyl-7-indolylamino)benzophenone (Compound 133),

7-Bromoindole(0.37 g, 1.9 mmol) was dissolved in dry DMF. $K_2CO_3$ (0.52 g, 3.8 mmol) and methyliodide (0.13 mL, 2.08 mmol) were added. The reaction was stirred at room temperature for 5 days, after which $H_2O$ (20 mL) was added, the water phase was extracted with $Et_2O$ (3×20 mL), and the combined organic phases were washed with brine, dried ($MgSO_4$), filtered and concentrated in vacuo. The crude product was purified by chromatography, eluent EtOAc:petroleum ether 1:20 to give 7-bromo-1-methylindole as a crystalline compound.

$^{13}$C NMR (CDCl$_3$): δ 133.07, 131.75, 126.54, 120.46, 120.34, 103.89, 101.18, 36.84.

Compound 133 was prepared according to

General Procedure: 1

Starting compound II: 7-bromo-1-methylindole (0.23 g, 1.1 mmol)

Starting compound III: 4-amino-2-chloro-2'-methylbenzophenone (compound 2) (0.25 g, 1.0 mmol)

Solvent: 1,4-dioxane (6 mL)

Base: t-BuONa

Reaction time: 18 h

Reaction temperature: 100° C.

Purification: Chromatography using EtOAc:petroleum ether 1:3

Product: compound 133, 0.23 g amorphous compound.

$^{13}$C NMR (CDCl$_3$): δ 196.55, 151.82, 139.37, 137.71, 135.36, 133.85, 132.97, 131.62, 131.19, 131.05, 130.68, 129.50, 127.92, 125.30, 123.76, 121.83, 120.53, 120.19, 115.06, 111.34, 101. 50, 35.49, 20.35.

EXAMPLE 34

2-Chloro-2'-methyl-4-(1-methyl-5-indolylamino)benzophenone (Compound 134),

5-Bromo-1-methylindole was prepared from 5-bromoindole as described for the preparation of 7-bromo-1-methylindole from 7-bromoindole. Purification by chromatography using EtOAc:petroleum ether 1:10

$^{13}$C NMR (CDCl$_3$): δ 135.37, 130.12, 129.94, 124.30, 123.27, 112.66, 110.63, 100.53, 32.96.

Compound 134 was prepared according to

General Procedure: 1

Starting compound II: 5-bromo-1-methylindole (0.23 g, 1.1 mmol)

Starting compound III: 4-amino-2-chloro-2'-methylbenzophenone (compound 2) (0.25 g, 1.0 mmol)

Solvent: 1,4-dioxane (6 mL)

Base: t-BuONa

Reaction time: 18 h

Reaction temperature: 100° C.

Purification: Chromatography using EtOAc:petroleum ether 1:3

Product: compound 134, 0.12 g crystalline compound.

$^{13}$C NMR (CDCl$_3$): δ 7.45(d,1H), 7.36–7.18(m,6H), 7.08 (d,1H), 7.06(dd,1H), 6.82(d,1H), 6.66(dd,1H), 6.45(dd,1H), 6.01(s,1H), 3.80(s.3H), 2.41(s,3H).

EXAMPLE 35

2-Chloro-2',5'-dimethyl-4-(4-methyl-3-pyridylamino)benzophenone (Compound 135)

General Procedure: 1

Starting compound II: 3-Bromo-4-methylpyridine (0.092 g, 0.5 mmol)

Starting compound III: 4-Amino-2-Chloro-2',5'-dimethylbenzophenone (0.134 g, 0.5 mmol)

Solvent: 1,4-dioxan (5 mL)

Base: t-BuONa

Reaction time: 6 h

Reaction temperature: 100° C.

Purification: Flash chromatography using $CH_2Cl_2$:acetone 9:1

Product: Compound 135, 0.078 g oil. $^{13}$C NMR (CDCl$_3$): δ 196.7, 148.4, 146.5, 146.0, 142.1, 138.9, 135.5, 135.1, 134.9, 134.8, 133.5, 131.7, 131.2, 130.1, 129.4, 125.9, 116.0, 112.3, 20.8, 19.9, 17.5.

EXAMPLE 36

2-Chloro-2',5'-dimethyl-4-(4-isoquinolylamino)benzophenone (Compound 136)

General Procedure: 1

Starting compound II: 4-Bromoisoquinoline (0.103 g, 0.49 mmol)

Starting compound III: 4-Amino-2-Chloro-2',5'-dimethylbenzophenone (0.131 g, 0.5 mmol)

Solvent: 1,4-dioxan (5 mL)

Base: t-BuONa

Reaction time: 4 h

Reaction temperature: 100° C.

Purification: Flash chromatography using EtOAc:petroleum ether 1:1

Product: Compound 136, 0.18 g crystalline compound.

$^{13}$C NMR (CDCl$_3$): δ 196.8, 150.1, 149.2, 139.0, 138.6, 135.1, 134.9, 134.8, 133.5, 132.1, 131.7, 131.2, 131.1, 130.8, 130.1, 129.4, 129.3, 128.2, 127.9, 121.6, 116.4, 112.6, 20.8, 20.0.

EXAMPLE 37

2-Chloro-4-(4-isoquinolylamino)-2',4',5'-trimethylbenzophenone (Compound 137)

General Procedure: 1

Starting compound II: 4-Bromoisoquinoline (0.103 g, 0.49 mmol)

Starting compound III: 4-Amino-2-chloro-2',4',5'-trimethylbenzophenone (0.148 g, 0.5 mmol)

Solvent: 1,4-dioxan (5 mL)

Base: t-BuONa

Reaction time: 6 h

Reaction temperature: 100° C.

Purification: Flash chromatography using $CH_2Cl_2$:acetone 9:1

Product: Compound 137, 0.16 g crystalline compound.

$^{13}$C NMR (CDCl$_3$): δ 196.6, 149.9, 148.9, 140.3, 138.3, 136.2, 135.8, 134.6, 133.5, 133.0, 132.8, 132.0, 131.5, 131.3, 130.7, 130.0, 129.3, 128.1, 127.8, 121.6, 116.4, 112.7, 20.1, 19.7, 19.1.

EXAMPLE 38

2,3'-Dichloro-2'-methyl-4-(4-methyl-3-pyridylamino)benzophenone (Compound 138)

General Procedure: 1

Starting compound II: 3-Bromo-4-methylpyridine (0.095 g, 0.5 mmol)
Starting compound III: 4-Amino-2,3'-dichloro-2'-methylbenzophenone (0.144 g, 0.5 mmol)
Solvent: 1,4-dioxan (5 mL)
Base: t-BuONa
Reaction time: 6 h
Reaction temperature: 100° C.
Purification: Flash chromatography using $CH_2Cl_2$:acetone 9:1
Product: Compound 138, 0.09 g oil.
$^{13}$C NMR ($CDCl_3$): δ 195.3, 149.2, 146.8, 146.4, 142.5, 142.0, 135.9, 135.8, 135.1, 134.9, 134.3, 131.2, 127.9, 126.9, 126.4, 126.0, 116.0, 112.1, 17.5, 17.1.

EXAMPLE 39

2-Fluoro-2'-methyl-4-(4-methyl-3-pyridylamino)benzophenone (Compound 139)

General Procedure: 1

Starting compound II: 3-Bromo-4-methylpyridine (0.092 g, 0.5 mmol)
Starting compound III: 4-Amino-2-fluoro-2'-methylbenzophenone (0.120 g, 0.5 mmol)
Solvent: 1,4-dioxan (5 mL)
Base: t-BuONa
Reaction time: 6 h
Reaction temperature: 100° C.
Purification: Flash chromatography using EtOAc:petroleum ether 1:1
Product: Compound 139, 0.02 g oil.
$^{13}$C NMR ($CDCl_3$): δ 194.3, 163.7, 151.3, 146.8, 146.6, 142.8, 140.3, 136.3, 135.2, 134.0, 130.9, 130.2, 128.1, 126.0, 125.3, 117.9, 109.9, 101.1, 19.9, 17.4.

EXAMPLE 40

2,4'-Dichloro-2'-methyl-4-(4-methyl-3-pyridylamino)benzophenone (Compound 140)

General Procedure: 1

Starting compound II: 3-Bromo-4-methylpyridine (0.086 g, 0.5 mmol)
Starting compound III: 4-Amino-2,4'dichloro-2'-methylbenzophenone (0.132 g, 0.47 mmol)
Solvent: 1,4-dioxan (5 mL)
Base: t-BuONa
Reaction time: 6 h
Reaction temperature: 100° C.
Purification: Flash chromatography using $CH_2Cl_2$:acetone 9:1
Product: Compound 140, 0.12 g oil.
$^{13}$C NMR ($CDCl_3$): δ 195.4, 148.7, 146.7, 146.2, 142.2, 140.1, 137.4, 136.8, 135.3, 135.2, 133.4, 131.3, 131.1, 128.9, 125.9, 125.6, 115.8, 112.4, 20.4, 17.5.

EXAMPLE 41

2-Chloro-4'-fluoro-4-(4-isoquinolylamino)-2'-methylbenzophenone (Compound 141)

General Procedure: 1

Starting compound II: 4-Bromoisoquinoline (0.104 g, 0.5 mmol)
Starting compound III: 4-Amino-2-chloro-4'-fluoro-2'-methylbenzophenone (0.140 g, 0.53 mmol)
Solvent: 1,4-dioxan (5 mL)
Base: t-BuONa
Reaction time: 6 h
Reaction temperature: 100° C.
Purification: Flash chromatography using $CH_2Cl_2$:acetone 9:1
Product: Compound 141, 0.13 g crystalline compound.
$^{13}$C NMR ($CDCl_3$): δ 195.4, 164.0, 150.3, 149.3, 141.8, 138.7, 135.0, 134.9, 133.1, 132.4, 132.4, 131.0, 130.8, 129.4, 129.3, 128.2, 127.9, 121.6, 118.2, 116.2, 112.7, 112.3, 20.8.

EXAMPLE 42

4'-n-Butyl-2-chloro-4-(4-isoquinolylamino)-2'-methylbenzophenone (Compound 142)

General Procedure: 1

Starting compound II: 4-Bromoisoquinoline (0.104 g, 0.5 mmol)
Starting compound III: 4-Amino-2'-n-butyl-2-chloro-2'-methylbenzophenone (0.150 g, 0.5 mmol)
Solvent: 1,4-dioxan (5 mL)
Base: t-BuONa
Reaction time: 6 h
Reaction temperature: 100° C.
Purification: Flash chromatography using $CH_2Cl_2$:acetone 9:1
Product: Compound 142, 0.17 g oil.
$^{13}$C NMR ($CDCl_3$): δ 196.4, 150.0, 148.8, 146.7, 138.6, 138.5, 136.0, 134.7, 133.0, 132.1, 131.7, 131.2, 130.8, 130.7, 130.1, 129.3, 128.2, 127.9, 125.4, 121.6, 116.3, 112.7, 35.6, 33.3, 22.4, 20.8, 13.9.

EXAMPLE 43

2-Chloro-4-(5-isoquinolylamino)-2'-methylbenzophenone (Compound 143)

General Procedure: 1

Starting compound II: 5-Bromoisoquinoline (0.104 g, 0.5 mmol)
Starting compound III: 4-Amino-2-chloro-2'-methylbenzophenone (compound 2) (0.122 g, 0.5 mmol)
Solvent: 1,4-dioxan (5 mL)
Base: t-BuONa
Reaction time: 6 h
Reaction temperature: 100° C.
Purification: Flash chromatography using $CH_2Cl_2$:acetone 9:1
Product: Compound 143, 0.16 g oil.
$^{13}$C NMR ($CDCl_3$): δ 196.6, 153.0, 148.7, 143.4, 138.9, 138.0, 135.5, 135.0, 133.5, 131.6, 131.3, 131.0, 129.8, 129.5, 127.4, 125.4, 124.8, 123.8, 116.6, 115.1, 113.0, 20.5.

EXAMPLE 44

2-Chloro-4-(4-isoquinolylamino)-4'-methoxy-2'-methylbenzophenone (Compound 144)

General Procedure: 1

Starting compound II: 4-Bromoisoquinololine (0.104 g, 0.5 mmol)
Starting compound III: 4-Amino-2-chloro-4'-methoxy-2'-methylbenzophenone (0.136 g, 0.5 mmol)
Solvent: 1,4-dioxan (5 mL)
Base: t-BuONa
Reaction time: 6 h
Reaction temperature: 100° C.
Purification: Flash chromatography using $CH_2Cl_2$:acetone 9:1
Product: Compound 144, 0.19 g crystalline compound.
$^{13}C$ NMR ($CDCl_3$): δ 195.5, 161.9, 149.9, 148.5, 142.0, 138.3, 134.2, 133.7, 132.4, 132.0, 131.4, 130.9, 130.7, 129.3, 128.2, 127.8, 121.6, 117.1, 116.3, 112.9, 110.4, 55.3, 21.5.

EXAMPLE 45

2-Fluoro-4-(4-isoquinolylamino)-4'-methoxy-2'-methylbenzophenone (Compound 145)

General Procedure: 1

Starting compound II: 4-Bromoisoquinoline (0.103 g, 0.5 mmol)
Starting compound III: 4-Amino-2-fluoro-4'-methoxy-2'-methylbenzophenone (0.130 g, 0.5 mmol)
Solvent: 1,4-dioxan (5 mL)
Base: t-BuONa
Reaction time: 6 h
Reaction temperature: 100° C.
Purification: Flash chromatography using EtOAc: petroleum ether 1:1 followed by recrystallization from EtOAc.
Product: Compound 145, 0.07 g crystalline compound.
$^1H$ NMR (DMSO-$D_6$): δ 9.18 (s,1H), 9.13 (s,1H), 8.54 (s,1H), 8.20 (d,1H), 8.03 (d,1H), 7.83 (t,1H), 7.75 (t,1H), 7.42 (t,1H), 7.30 (d,1H), 6.87 (d,1H), 6.81 (dd,1H), 6.77 (dd,1H), 6.58 (dd,1H), 3.80 (s,3H), 2.34 (s,3H).

EXAMPLE 46

2,4'-Dichloro-2'-methyl-4-(1-methyl-7-indolylamino)benzophenone (Compound 146)

General Procedure: 1

Starting compound II: 7-Bromo-1-methylindole (0.115 g, 0.55 mmol) prepared as described in example 33
Starting compound III: 4-Amino-2,4'-dichloro-2'-methylbenzophenone (0.140 g, 0.5 mmol)
Solvent: 1,4-dioxan (5 mL)
Base: t-BuONa
Reaction time: 6 h
Reaction temperature: 100° C.
Purification: Flash chromatography using EtOAc:petroleum ether 1:3
Product: Compound 146, 0.08 g crystalline compound.
$^{13}C$ NMR ($CDCl_3$): δ 195.5, 152.1, 139.8, 137.8, 136.5, 135.4, 133.8, 132.9, 131.6, 131.2, 131.1, 130.8, 127.5, 125.5, 123.6, 121.8, 120.6, 120.2, 115.0, 111.4, 101.5, 35.5, 20.2.

EXAMPLE 47

2-Chloro-4-(1-methyl-7-indolylamino)-2',4',5'-trimethylbenzophenone (Compound 147)

General Procedure: 1

Starting compound II: 7-Bromo-1-methylindole (0.115 g, 0.55 mmol) prepared as described in example 33
Starting compound III: 4-Amino-2-chloro-2',4',5'-trimethylbenzophenone (0.137 g, 0.5 mmol)
Solvent: 1,4-dioxan (5 mL)
Base: t-BuONa
Reaction time: 6 h
Reaction temperature: 100° C.
Purification: Flash chromatography using EtOAc:petroleum ether 1:3
Product: Compound 147, 0.097 g crystalline compound.
$^{13}C$ NMR ($CDCl_3$): δ 196.6, 151.5, 140.0, 136.6, 135.5, 135.0, 133.5, 133.4, 133.0, 132.7, 131.6, 131.3, 131.0, 128.6, 124.0, 121.8, 120.4, 120.2, 115.0, 111.3, 101.5, 35.5, 20.0, 19.7, 19.1.

EXAMPLE 48

2-Chloro-2',5'-dimethyl-4-(1-methyl-7-indolylamino)benzophenone (Compound 148)

General Procedure: 1

Starting compound II: 7-Bromo-1-methylindole (0.115 g, 0.55 mmol) prepared as described in example 33
Starting compound III: 4-Amino-2-chloro-2',5'-dimethylbenzophenone (0.148 g, 0.5 mmol)
Solvent: 1,4-dioxan (5 mL)
Base: t-BuONa
Reaction time: 6 h
Reaction temperature: 100° C.
Purification: Flash chromatography using EtOAc:petroleum ether 1:3
Product: Compound 148, 0.30 g crystalline compound.
$^1H$ NMR ($CDCl_3$): δ 7.56 (d,1H), 7.28 (d,1H), 7.17–7.02 (m,4H), 6.98 (d,1H), 6.95 (d,1H), 6.61 (d,1H), 6.50 (d,1H), 6.42 (dd,1H), 5.93 (s,Br,1H), 3.81 (s,3H), 2.32 (s,3H), 2.27 (s,3H).

EXAMPLE 49

2-Chloro-4-(3-ethoxy-4-isoquinolylamino)-2'-methylbenzophenone (Compound 149)

General Procedure: 1

Starting compound II: 4-Bromo-3-ethoxyisoquinoline (0.097 g, 0.39 mmol)
Starting compound III: 4-Amino-2-chloro-2'-methylbenzophenone (compound 2) (0.095 g, 0.39 mmol)
Solvent: 1,4-dioxan (3 mL)
Base: t-BuONa
Reaction time: 6 h
Reaction temperature: 100° C.
Purification: Flash chromatography using EtOAc:petroleum ether 1:3
Product: Compound 149, 0.11 g crystalline compound.
$^{13}C$ NMR ($CDCl_3$): δ 196.6, 155.1, 149.9, 147.4, 139.3, 137.8, 134.8, 133.3, 131.2, 130.7, 130.5, 129.6, 128.7, 128.1, 125.6, 125.3, 124.5, 121.9, 116.2, 113.9, 112.4, 62.7, 20.4, 15.0.

EXAMPLE 50

2-Chloro-4-(1-ethoxy-4-isoquinolylamino)-2'-methylbenzophenone (Compound 150)

General Procedure: 1

Starting compound II: 4-Bromo-1-ethoxyisoquinoline (0.097 g, 0.39 mmol)

Starting compound III: 4-Amino-2-chloro-2'-methylbenzophenone (compound 2) (0.095 g, 0.39 mmol)

Solvent: 1,4-dioxan (3 mL)

Base: t-BuONa

Reaction time: 6 h

Reaction temperature: 100° C.

Purification: Flash chromatography using EtOAc:petroleum ether 1:3

Product: Compound 150, 0.11 g crystalline compound.

$^{13}$C NMR (CDCl$_3$): δ 196.5, 159.7, 151.2, 139.4, 138.5, 137.7, 135.5, 135.3, 133.8, 131.2, 131.0, 130.7, 129.5, 128.0, 127.1, 125.3, 125.0, 124.6, 121.8, 120.3, 115.1, 111.4, 62.4, 20.4, 14.6.

EXAMPLE 51

4-(2-Benzoxazolylamino)-2-chloro-2'-methylbenzophenone (Compound 151)

General Procedure: 1

Starting compound II: 2-Chlorobenzoxazole (0.35 mL, 3.0 mmol)

Starting compound III: 4-Amino-2-chloro-2'-methylbenzophenone (compound 2) (0.49 g, 2.0 mmol)

Solvent: 1,4-dioxan (5 mL)

Base: t-BuONa

Reaction time: 16 h

Reaction temperature: 100° C.

Purification: Flash chromatography using EtOAc:petroleum ether 1:4

Product: Compound 151, 0.17 g, crystalline compound.

$^{13}$C NMR (CDCl$_3$): δ 196.9, 157.3, 147.8, 141.4, 141.3, 138.7, 138.0, 134.0, 133.1, 132.2, 131.6, 130.6, 125.5, 124.7, 124.5, 122.6, 119.3, 117.4, 115.7, 109.5, 20.8.

EXAMPLE 52

4-(1-Methyl-2-benzimidazolylamino)-2-chloro-2'-methylbenzophenone (Compound 152)

General Procedure: 1

Starting compound II: 2-Chloro-1-methylbenzoimidazole (0.33 g, 2.0 mmol)

Starting compound III: 4-Amino-2-chloro-2'-methylbenzophenone (compound 2) (0.49 g, 2.0 mmol)

Solvent: 1,4-dioxan (5 mL)

Base: t-BuONa

Reaction time: 24 h

Reaction temperature: 100° C.

Purification: Flash chromatography using EtOAc:petroleum ether 1:2

Product: Compound 152, 0.27 g, crystalline compound $^{13}$C NMR (CDCl$_3$): δ 196.0, 147.0, 140.4, 139.0, 137.1, 135.4, 133.9, 132.0, 131.8, 130.9, 129.8, 125.6, 125.4, 124.6, 121.1, 117.6, 113.7, 110.1, 31.3, 20.9.

EXAMPLE 53

4-(2-Benzothiazolylamino)-2-chloro-2'-methylbenzophenone (Compound 153)

General Procedure: 1

Starting compound II: 2-Chlorobenzothiazole (0.26 mL, 2.0 mmol)

Starting compound III: 4-Amino-2-chloro-2'-methylbenzophenone (compound 2) (0.49 g, 2.0 mmol)

Solvent: 1,4-dioxan (5 mL)

Base: t-BuONa

Reaction time: 20 h

Reaction temperature: 100° C.

Purification: Flash chromatography using acetone:CH$_2$Cl$_2$ 1:100

Product: Compound 153, 0.24 g, crystalline compound $^{13}$C NMR (CDCl$_3$): δ 196.9, 161.5, 151.1, 143.1, 138.7, 138.0, 134.1, 133.1, 132.3, 131.6, 130.5, 130.3, 126.5, 125.5, 123.4, 121.0, 120.3, 119.6, 116.0, 20.8.

EXAMPLE 54

2-Chloro-2'-methyl-4-(2-pyrimidylamino)benzophenone (Compound 154)

General Procedure: 1

Starting compound II: 2-Bromopyrimidine (0.18 g, 1.1 mmol)

Starting compound III: 4-Amino-2-chloro-2'-methylbenzophenone (compound 2) (0.25 g, 1.0 mmol)

Solvent: 1,4-dioxan (5 mL)

Base: t-BuONa

Reaction time: 18 h

Reaction temperature: 100° C.

Purification: Flash chromatography using acetone:CH$_2$Cl$_2$ 2:100

Product: Compound 154, 0.14 g, crystalline compound $^{13}$C NMR (CDCl$_3$): δ 196.8, 159.4, 158.1, 143.0, 138.4, 133.9, 132.1, 132.0, 131.5, 131.3, 130.3, 125.4, 119.8, 116.2, 113.8, 20.7.

EXAMPLE 55

2-Chloro-2'-methyl-4-(7-methyl-purin-6-ylamino)benzophenone (Compound 155)

General Procedure: 1

Starting compound II: 6-Bromo-7-methylpurine (0.18 g, 0.84 mmol)

Starting compound III: 4-Amino-2-chloro-2'-methylbenzophenone (compound 2) (0.19 g, 0.77 mmol)

Solvent: 1,4-dioxan (5 mL)

Base: t-BuONa

Reaction time: 18 h

Reaction temperature: 100° C.

Purification: Flash chromatography using EtOAc:petroleumether 1:3→1:0 followed by recrystallisation from Et$_2$O Product: Compound 155, 0.06 g crystalline compound $^{13}$C NMR (CDCl$_3$): δ 196.7, 152.7, 151.4, 150.4, 142.3, 141.8, 138.7, 138.2, 133.7, 133.1, 131.9, 131.6, 131.4, 130.5, 125.5, 120.7, 120.6, 117.1, 30.0, 20.8.

EXAMPLE 56

2-Chloro-2'-methyl-4-(2-methyl-5-benzothiazolylamino)benzophenone (Compound 156)

General Procedure: 1

Starting compound II: 5-Bromo-2-methylbenzothiazole (0.25 g, 1.1 mmol)
Starting compound III: 4-Amino-2-chloro-2'-methylbenzophenone (compound 2) (0.25 g, 1.0 mmol)
Solvent: 1,4-dioxan (6 mL)
Base: t-BuONa
Reaction time: 18 h
Reaction temperature: 100° C.
Purification: Flash chromatography using EtOAc:petroleumether 1:3→1:2
Product: Compound 156, 0.21 g oil
$^{13}$C NMR (CDCl$_3$): δ 196.5, 168.7, 154.6, 147.8, 139.1, 138.8, 138.0, 135.1, 133.4, 131.3, 130.9, 130.8, 129.8, 129.5, 125.4, 122.2, 119.3, 116.5, 114.3, 113.0, 20.5, 20.2.

EXAMPLE 57

2-Chloro-2'-methyl-4-(pyrazin-2-ylamino)benzophenone (Compound 157)

General Procedure: 1

Starting compound II: 2-Iodopyrazine (0.23 g, 1.1 mmol)
Starting compound III: 4-Amino-2-chloro-2'-methylbenzophenone (compound 2) (0.25 g, 1.0 mmol)
Solvent: 1,4-dioxan (6 mL)
Base: t-BuONa
Reaction time: 6 h
Reaction temperature: 100° C.
Purification: Flash chromatography using EtOAc:petroleum ether 1:1 followed by purification on RP HPLC
Product: Compound 157, oil
$^{13}$C NMR (CDCl$_3$): δ 196.8, 151.0, 143.2, 141.6, 138.6, 138.3, 136.3, 134.5, 134.0, 132.4, 132.2, 131.6, 131.4, 130.4, 125.5, 119.7, 116.1, 20.7.

EXAMPLE 58

2-Chloro-2'-methyl-4-(5-pyrimidylamino)benzophenone (Compound 158)

General Procedure: 1

Starting compound II: 5-Bromopyrimidine (0.18 g, 1.1 mmol)
Starting compound III: 4-Amino-2-chloro-2'-methylbenzophenone (compound 2) (0.25 g, 1.0 mmol)
Solvent: 1,4-dioxan (5 mL)
Base: t-BuONa
Reaction time: 6 h
Reaction temperature: 100° C.
Purification: Flash chromatography using EtOAc:petroleum ether 1:1→1:0 followed by purification on RP HPLC
Product: Compound 158, oil
$^{13}$C NMR (CDCl$_3$): δ 196.3, 153.3, 148.0, 145.0, 138.6, 138.2, 134.9, 133.0, 132.2, 131.6, 131.5, 130.2, 125.5, 117.7, 114.2, 20.7.

EXAMPLE 59

2-Chloro-2'-methyl-4-(5-nitro-2-thiazolylamino)benzophenone (Compound 159)

4-Amino-2-chloro-2'-methylbenzophenone (compound 2) (0.246 g, 1.0 mmol), 2-bromo-5-nitrothiazol (0.209 g, 1.0 mmol) and N,N-diisopropyl ethylamine (0.18 mL, 1.0 mmol) were mixed in a 4 mL screwcap vessel and kept at 60° C. for 18 h. The reaction mixture was partitioned between EtOAc and water, and the organic phase was washed with H$_2$O (3×10 mL) and brine (10 mL), dried (MgSO$_4$) and evaporated in vacuo. The crude compound was purified by flash chromatografy using EtOAc:CH$_2$Cl$_2$ 1:50 as the eluent.

Product: Compound 159, 0.12 g, crystalline compound.
$^{13}$C NMR (DMSO-D-6): δ 195.8, 166.5, 145.2, 142.1, 138.6, 137.8, 137.4, 133.1, 131.9, 131.8, 131.6, 130.3, 125.9, 119.3, 117.0, 54.9, 20.3.

EXAMPLE 60

2-Chloro-2'-methyl-4-((4-methyl-3-nitro-(1,2,4-triazol-5-ylamino))benzophenone (Compound 160)

Preparation of 5-Bromo-4-methyl-3-nitro-1,2,4-triazole

5-Bromo-3-nitro-1,2,4-triazole (0.78 g, 4.0 mmol) was dissolved in DMF (20 mL). K$_2$CO$_3$ (1.1 g, 8.0 mmol) and CH$_3$I (0.28 mL, 4.4 mmol) were added, and the mixture was stirred at room temperature for 18 h. H$_2$O was added, and the water phase was extracted three times with Et$_2$O. The combined organic phases were washed with brine, dried (MgSO$_4$) and evaporated, and the crude product was purified by flash chromatografy using EtOAc:petroleum ether 1:1 as the eluent
Product: 2-bromo-1-methyl-5-nitro-1,2,4-triazole, 0.44 g
$^{13}$C NMR (CDCl$_3$): δ 131.3, 80.6, 38.0.

Preparation of Compound 160

General Procedure: 1

Starting compound II: 5-Bromo-4-methyl-3-nitro-1,2,4-triazole (0.22 g, 1.1 mmol)
Starting compound III: 4-Amino-2-chloro-2'-methylbenzophenone (compound 2) (0.24 g, 1.0 mmol)
Solvent: Toluene (5 mL)
Base: Cs$_2$CO$_3$
Reaction time: 18 h
Reaction temperature: 100° C.
After 18 h an extra portion of BINAP (24 mg) and Pd2(dba)3 (17 mg) were added, and the reaction mixture was shaken another 24 h at 100° C.
Work up as described in General Procedure 1
Purification: Flash chromatography using EtOAc:petroleum ether 1:1 followed by purification on reversed phase HPLC
Product: Compound 160, oil
$^{13}$C NMR (DMSO-D-6): δ 195.8, 158.3, 151.0, 142.8, 137.8, 137.4, 131.9, 131.6, 131.4, 129.9, 125.8, 117.9, 115.6, 35.6, 20.1.

EXAMPLE 61

| Tablet containing compound 116 | |
|---|---|
| Compound 116 (active substance) | 50 mg |
| Lactose | 125 mg |
| Starch | 12 mg |
| Methyl cellulose | 2 mg |
| Sodium carboxymethyl cellulose | 10 mg |
| Magnesium stearate | 1 mg |

The active substance, lactose and starch are mixed to a homogeneous state in a suitable mixer and moistened with a 5 per cent aqueous solution of methyl cellulose 15 cps. The mixing is continued until granules are formed. If necessary, the wet granulation is passed through a suitable screen and dried to a water content of less than 1% in a suitable drier, e.g. fluid bed or drying oven. The dried granules are passed through a 1 mm screen and mixed to a homogeneous state with sodium carboxymethyl cellulose. Magnesium stearate is added, and the mixing is continued for a short period of time. Tablets with a weight of 200 mg are produced from the granulation by means of a suitable tabletting machine.

EXAMPLE 62

Formulation for Injection Containing Compound 116.

| Compound 116 (active substance) | 1% |
|---|---|
| Sodium chloride | q.s. |
| Ethanol | 10% |
| Water for injection to make | 100% |

The active substance is dissolved in ethanol (10%) then water for injection made isotonic with sodium chloride is added to make 100%. The mixture is filled into ampoules and sterilised.

EXAMPLE 63

Cream Formulation Containing Compound 116

Compound 116 (10 g) was dissolved in Octyldodecyl myristate (250 g) to form Part A. Methylparaben (1 g) and propylparaben (0.2 g) were dissolved in phenoxyethanol (6 g) and mixed with a 0.025 M Phosphate buffer pH=7.5 (632,8 g) to form Part B. Cetostearyl alcohol (50 g) and ARLACEL 165® (50 g) was melted in a vessel at 70° to 80° C. Part A was added and heated to 60–70° C. The aqueous phase was likewise heated to 60–70° C. and slowly added to the melted oil phase under high speed stirring. The homogenised components were cooled to room temperature.

I claim:
1. A compound of the formula I

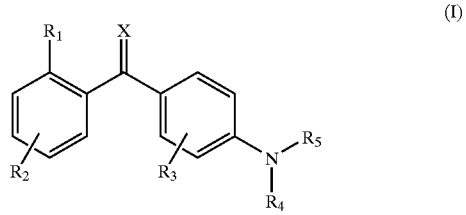

wherein $R_1$ is selected from the group consisting of halogen, haloalkyl, hydroxy, hydroxyalkyl, hydroxyalkyloxy, mercapto, cyano, carboxy, nitro, alkyl, alkenyl, alkynyl, cycloalkyl, cycloalkenyl, heterocycloalkyl, aryl, heteroaryl, aralkyl, alkylaryl, alkoxy, aralkoxy, alkylthio, alkoxycarbonyl, alkylcarbonyloxy, alkoxycarbonyloxy, alkylsulfonyloxy, alkyloxysulfonyl, alkylcarbonylamino, aminocarboaminoalkyl, aminosulfonyl, alkylsulfonylamino, alkanoyl, alkylcarbonyl, —$NR_9R_{10}$ or —$CONR_9R_{10}$, wherein $R_9$ and $R_{10}$ are the same or different and individually represent hydrogen, alkyl or aryl;

$R_2$ represents one or more, same or different substituents selected from the group consisting of hydrogen, halogen, haloalkyl, hydroxy, hydroxyalkyl, hydroxyalkyloxy, mercapto, cyano, carboxy, nitro, alkyl, alkenyl, alkynyl, cycloalkyl, cycloalkenyl, heterocycloalkyl, aryl, heteroaryl, aralkyl, alkylaryl, alkoxy, aralkoxy, alkylthio, alkoxycarbonyl, alkylcarbonyloxy, alkoxycarbonyloxy, alkylsulfonyloxy, alkyloxysulfonyl, alkylcarbonylamino, aminocarboaminoalkyl, aminosulfonyl, alkylsulfonylamino, alkanoyl, alkylcarbonyl, —$NR_9R_{10}$ or —$CONR_9R_{10}$, wherein $R_9$ and $R_{10}$ are the same or different and individually represent hydrogen, alkyl or aryl;

$R_3$ represents one or more, same or different substituents selected from the group consisting of hydrogen, halogen, haloalkyl, hydroxy, hydroxyalkyl, mercapto, cyano, nitro, alkyl, alkenyl, alkynyl, cycloalkyl, aryl, aralkyl, alkylaryl, alkoxy, aralkoxy, alkylthio, alkoxycarbonyl, alkylcarbonylamino, alkylcarbonyloxy, alkoxycarbonyloxy, alkylcarbonyl —$NR_9R_{10}$ or —$CONR_9R_{10}$ wherein $R_9$ and $R_{10}$ are the same or different and individually represent hydrogen, alkyl or aryl;

$R_4$ represents hydrogen, alkyl, alkenyl, alkynyl, cycloalkyl, cycloalkenyl, carboxy or aryl;

$R_5$ represents a heteroaromatic mono- or bicyclic ring system comprising 1–4 heteroatoms, except for triazine, the ring system being optionally substituted by hydrogen, halogen, haloalkyl, hydroxy, hydroxyalkyl, hydroxyalkyloxy, mercapto, cyano, carboxy, nitro, alkyl, alkenyl, alkynyl, cycloalkyl, cycloalkenyl, heterocycloalkyl, aryl, heteroaryl, aralkyl, alkylaryl, alkoxy, aralkoxy, alkylthio, alkoxycarbonyl, alkylcarbonyloxy, alkoxycarbonyloxy, alkylsulfonyloxy, alkyloxysulfonyl, alkylcarbonylamino, aminocarboaminoalkyl, aminosulfonyl, alkylsulfonylamino, alkanoyl, alkylcarbonyl, —$NR_9R_{10}$ or —$CONR_9R_{10}$, wherein $R_9$ and $R_{10}$ are the same or different and individually represent hydrogen, alkyl or aryl;

X represents oxygen, sulphur, N—OH or $NR_{11}$ wherein $R_{11}$ is hydrogen or alkyl;

and salts thereof with pharmaceutically acceptable acids, hydrates and solvates, and optionally the N-oxides thereof wherein a nitrogen atom of the heterocyclic $R_5$ substituent is oxidised.

2. A compound according to claim 1, wherein $R_1$ represents a substituent selected from the group consisting of halogen, hydroxy, mercapto, trifluoromethyl, amino, $(C_1–C_6)$alkyl, $(C_2–C_6)$alkenyl, $(C_1–C_6)$alkoxy, $(C_1–C_6)$alkylthio, $(C_1–C_6)$alkylamino, $(C_1–C_6)$alkoxycarbonyl, cyano, —$CONH_2$, phenyl, and nitro.

3. A compound according to claim 1, wherein $R_2$ represents one or more, same or different substituents selected from the group consisting of hydrogen, halogen, hydroxy, mercapto, trifluoromethyl, amino, $(C_1–C_6)$alkyl, $(C_2–C_6)$alkenyl, $(C_1–C_6)$alkoxy, $(C_1–C_6)$alkylthio, $(C_1–C_6)$alkylamino, $(C_1–C_6)$alkoxycarbonyl, cyano, —$CONH_2$, phenyl, and nitro.

4. A compound according to claim 1, wherein $R_3$ represents one or more, same or different substituents selected from the group consisting of hydrogen, halogen, hydroxy, mercapto, trifluoromethyl, amino, $(C_1–C_6)$alkyl, $(C_2–C_6)$alkenyl, $(C_1–C_6)$alkoxy, $(C_1–C_6)$alkylthio, $(C_1–C_6)$alkylamino, $(C_1–C_6)$alkoxycarbonyl, cyano, —$CONH_2$, phenyl, and nitro.

5. A compound according to claim 1, wherein $R_4$ represents hydrogen, $(C_1–C_6)$alkyl, $(C_2–C_6)$alkenyl, or $(C_3–C_6)$ cycloalkyl or -cycloalkenyl.

6. A compound according to claim 1, wherein $R_5$ represents an optionally substituted heteroaromatic ring system having one or 2 fused rings of 5 or 6 ring atoms and comprising 1 or 2 nitrogen atoms.

7. A compound according to claim 6 wherein $R_5$ is selected from the group consisting of

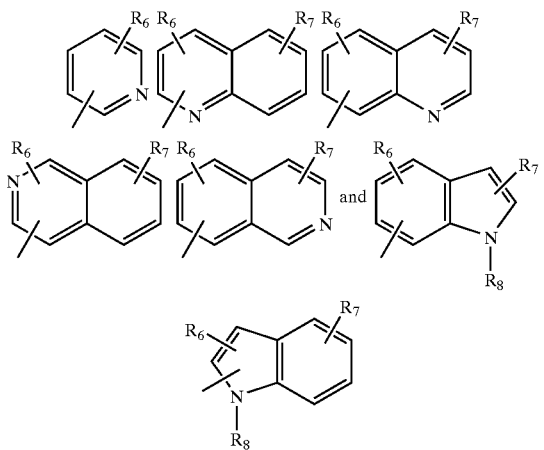

wherein $R_6$ and $R_7$ represent one or more, same or different substituents selected from the group consisting of hydrogen, halogen, hydroxy, mercapto, trifluoromethyl, cyano, carboxy, carbamoyl, amino, nitro, $(C_1–C_{10})$alkyl, $(C_2–C_{10})$alkenyl, $(C_3–C_8)$cycloalkyl or -cycloalkenyl, $(C_1–C_{10})$alkoxy, $(C_1–C_{10})$alkylthio, $(C_1–C_{10})$alkoxycarbonyl, and phenyl; and $R_8$ represents hydrogen, $(C_1–C_6)$alkyl, $(C_2–C_6)$alkenyl, or $(C_3–C_6)$cycloalkyl or -cycloalkenyl; and wherein $R_5$ is optionally oxidised to the corresponding N-oxide as exemplified herein.

8. A compound according to claim 1, wherein X represents oxygen, sulphur or NH.

9. A compound according to claim 7, wherein $R_6$ and $R_7$ represent one or more, same or different substituents selected from the group consisting of hydrogen, fluoro, chloro, bromo, hydroxy, trifluoromethyl, amino, $(C_1–C_6)$ alkyl, $(C_2–C_6)$alkenyl, $(C_1–C_6)$alkoxy, $(C_1–C_6)$ alkoxycarbonyl, cyano, carboxy, and —$CONH_2$.

10. A compound according to claim 7, wherein $R_8$ represents hydrogen, $(C_1–C_4)$alkyl, and $(C_2–C_6)$alkenyl.

11. A compound according to claim 10, wherein $R_8$ represents hydrogen, methyl, ethyl, allyl, propyl, benzyl, or t-butyl.

12. A compound according to claim 2 wherein $R_1$ represents a substituent selected from the group consisting of fluoro, chloro, bromo, hydroxy, methyl, and methoxy.

13. A compound according to claim 3 wherein $R_2$ represents one or more, same or different substituents selected from the group consisting of hydrogen, fluoro, chloro, bromo, hydroxy, trifluoromethyl, methyl, ethyl, and methoxy.

14. A compound according to claim 4 wherein $R_3$ represents one or more, same or different substituents selected from the group consisting of hydrogen, fluoro, chloro, bromo, hydroxy, methyl, and methoxy.

15. A compound according to claim 5 wherein $R_4$ represents hydrogen, methyl, or ethyl.

16. A compound according to claim 6 wherein $R_5$ is selected from the group consisting of substituted or non-substituted 3-pyridyl, 2-pyridyl, 3-quinolyl, 4-isoquinolyl, 4-indolyl, 5-indolyl, 6-indolyl or 7-indolyl moieties, and the corresponding N-oxides.

17. A compound according to claim 7 wherein $R_6$ and $R_7$ represents one or more, same or different substituents selected from the group consisting of hydrogen, fluoro, chloro, bromo, hydroxy, methyl, methoxy, cyano, and carboxy.

18. A compound according to claim 8 wherein X represents oxygen.

19. A compound according to claim 7 wherein at least one of $R_1$, $R_2$, $R_3$, $R_6$ and $R_7$ represents a phenyl group optionally substituted by hydroxy, amino, nitro, cyano, halogen, methyl or methoxy.

20. A compound according to claim 1 wherein said halogen is selected form the group consisting of fluoro, chloro, and bromo.

21. A compound according to claim 1 of the formula Ic:

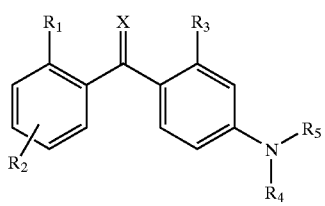

(Ic)

wherein $R_1$, $R_2$, $R_4$, $R_5$, $R_6$ and X have the meaning specified in formula I, and $R_3$ represents $(C_1–C_3)$ alkyl, fluoro, chloro, bromo, methoxy, and hydroxy, and salts thereof with pharmaceutically acceptable acids, hydrates and solvates.

22. A compound of the formula Ic, in which $R_1$ represents methyl or halogen; $R_2$ represents one or more substituents, and $R_3$ represents methyl, methoxy or chloro.

23. A compound according to claim 22 wherein $R_3$ represents a halogen atom.

24. A compound according to claim 23 wherein $R_3$ represents chlorine.

25. A compound according to claim 1 of formula I selected from the group consisting of:
   2-Chloro-2'-methyl-4-(4-pyridylamino)benzophenone (Compound 101), 2-Chloro-2'-methyl-4-(2-pyridylamino)benzophenone (Compound 102),
2-Chloro-2'-methyl-4-(5-nitro-2-pyridylamino) benzophenone (Compound 103),
4-(6-Amino-5-nitro-2-pyridylamino)-2-chloro-2'-methylbenzophenone (Compound 104),
6-Chloro-2-(3-chloro-4-(2-methylbenzoyl)phenylamino) isonicotinic acid (Compound 105),
4-(6-carbonitrile-2-pyridylamino)-2-chloro-2'-methylbenzophenone (Compound 106),
2-Chloro-2'-methyl-4-(3-pyridylamino)benzophenone (Compound 107),
2-Chloro-4-(5,6-diamino-2-pyridylamino)-2'-methylbenzophenone (Compound 108),
2-Chloro-2'-methyl-4-(3-nitro-2-pyridylamino) benzophenone (Compound 109),
4-(3-Amino-2-pyridylamino)-2-chloro-2'-methylbenzophenone (Compound 110),
4-(5-Amino-2-pyridylamino)-2-chloro-2'-methylbenzophenone (Compound 111),
2-Chloro-4-(4-isoquinolylamino)-2'-methylbenzophenone (Compound 114),
t-Butyl 5-(3-chloro-4-(2-methylbenzoyl)phenylamino) nicotinoate (Compound 115),
2-Chloro-2'-methyl-4-(4-methyl-3-pyridylamino) benzophenone (Compound 116),
2-Chloro-2'-methyl-4-(6-methyl-3-pyridylamino) benzophenone (Compound 117),
4-(5-Bromo-3-pyridylamino)-2-chloro-2'-methylbenzophenone (Compound 118),
4-(5-Carbonitrile-3-pyridylamino)-2-chloro-2'-methylbenzophenone (Compound 119),
4-(3-Bromo-2-pyridylamino)-2-chloro-2'-methylbenzophenone (Compound 120),
2-Chloro-2'-methyl-4-(8-quinolylamino)benzophenone (Compound 121),
2-Chloro-4-(6-ethoxy-3-pyridylamino)-2'-methylbenzophenone (Compound 122),
4-(4-Bromo-3-isoquinolylamino)-2-chloro-2'-methylbenzophenone (Compound 123),
2-Chloro-2'-methyl-4-(2-methyl-5-trifluoromethyl-3-pyridylamino)benzophenone (Compound 124),
2-Chloro-2'-methyl-4-(3-quinolylamino)benzophenone (Compound 125),
2-Chloro-4-(4-ethoxy-3-pyridylamino)-2'-methylbenzophenone (Compound 126),
2-Chloro-4-(2-ethoxy-3-pyridylamino)-2'-methylbenzophenone (Compound 127),
2-Chloro-2'-methyl-4-(2-methyl-6-quinolylamino) benzophenone (Compound 129),
2-Chloro-2'-methyl-4-(2-quinolylamino)benzophenone (Compound 131),
2-Chloro-4-(7-chloro-4-quinolylamino)-2'-methylbenzophenone (Compound 130),
2-Chloro-2'-methyl-4-(4-quinolylamino)benzophenone (Compound 132),
2-Chloro-2'-methyl-4-(1-methyl-7-indolylamino) benzophenone (Compound 133),
2-Chloro-2'-methyl-4(1-methyl-5-indolylamino) benzophenone (Compound 134),
2-Chloro-2',5'-dimethyl-4-(4-methyl-3-pyridylamino) benzophenone (Compound 135),
2-Chloro-21,51-dimethyl-4-(4-isoquinolylamino) benzophenone (Compound 136),
2-Chloro-4-(4-isoquinolylamino)-2',4',5'-trimethylbenzophenone (Compound 137),
2,3'-Dichloro-2'-methyl-4-(4-methyl-3-pyridylamino) benzophenone (Compound 138),
2-Fluoro-2'-methyl-4-(4-methyl-3-pyridylamino) benzophenone (Compound 139),
2,4'-Dichloro-2'-methyl-4-(4-methyl-3-pyridylamino) benzophenone (Compound 140),
2-Chloro-4'-fluoro-4-(4-isoquinolylamino)-2'-methylbenzophenone (Compound 141),
4'-n-Butyl-2-chloro-4-(4-isoquinolylamino)-2'-methylbenzophenone (Compound 142),
2-Chloro-4-(5-isoquinolylamino)-2'-methylbenzophenone (Compound 143),
2-Chloro-4-(4-isoquinolylamino)-4'-methoxy-2'-methylbenzophenone (Compound 144),
2-Fluoro-4-(4-isoquinolylamino)-4'-methoxy-2'-methylbenzophenone (Compound 145),
2,4'-Dichloro-2'-methyl-4-(1-methyl-7-indolylamino) benzophenone (Compound 146),
2-Chloro-4-(5-methyl-7-indolyamino)-2',4',5'-trimethylbenzophenone (Compound 147),
2-Chloro-2',5'-dimethyl-4-(1-methyl-7-indolylamino) benzophenone (Compound 148),
2-Chloro-4-(3-ethoxy-4-isoquinolylamino)-2'-methylbenzophenone (Compound 149),
2-Chloro-4-(1-ethoxy-4-isoquinolylamino)-2'-methylbenzophenone (Compound 150),
4-(2-Benzoxazolylamino)-2-chloro-2'-methylbenzophenone (Compound 151),
4-(2-Methyl-2-benzimidazolylamino)-2-chloro-2'-methylbenzophenone (Compound 152),
4-(2-Benzothiazolylamino)-2-chloro-2'-methyl benzophenone (Compound 153),
2-Chloro-2'-methyl-4-(2-pyrimidylamino)benzophenone (Compound 154),
2-Chloro-2'-methyl-4-(7-methyl-purin-6-ylamino) benzophenone (Compound 155),
2-Chloro-2'-methyl-4-(2-methyl-5-benzothiazolylamino) benzophenone (Compound 156),
2-Chloro-2'-methyl-4-(pyrazin-2-ylamino)benzophenone (Compound 157),
and 2-Chloro-2'-methyl-4-(5-pyrimidylamino) benzophenone (Compound 158);
and the N-oxides thereof wherein the nitrogen atom of the heterocyclic $R_5$ substituent is specifically oxidised, including the N-oxides:
2-Chloro-2'-methyl-4((2-pyridyl-N-oxide)amino) benzophenone (Compound 112),
2-Chloro-2'-methyl-4((3-pyridyl-N-oxide)amino) benzophenone (Compound 113),
2-Chloro-4((4-isoquinolyl-N-oxide)amino)-2'-methylbenzophenone (Compound 128),
and salts thereof with pharmaceutically acceptable acids, hydrates and solvates.

26. A compound according to claim 1 of the formula Ia or Ib

Ia

Ib wherein $R_1$, $R_2$, $R_3$, $R_4$ and $R_5$ have the meaning specified for formula I, and salts thereof with pharmaceutically acceptable acids, hydrates and solvates.

27. A compound according to claim 26 of formula Ia selected from the group consisting of:

2-Chloro-2'-methyl-4-(4-pyridylamino)thiobenzophenone,
2-Chloro-2'-methyl-4-(2-pyridylamino)thiobenzophenone,
2-Chloro-2'-methyl-4-(5-nitro-2-pyridylamino)thiobenzophenone,
4-(6-Amino-5-nitro-2-pyridylamino)-2-chloro-2'-methyl((thiobenzophenone),
6-Chloro-2-(3-chloro-4-(2-methylthiobenzoyl)phenylamino)isonicotinic acid,
4-(6-carbonitrile-2-pyridylamino)-2-chloro-2'-methyl(thiobenzophenone),
2-Chloro-2'-methyl-4-(3-pyridylamino)thiobenzophenone,
2-Chloro-4-(5,6-diamino-2-pyridylamino)-2'-methyl(thiobenzophenone),
2-Chloro-2'-methyl-4-(3-nitro-2-pyridylamino)thiobenzophenone,
4-(3-Amino-2-pyridylamino)-2-chloro-2'-methyl(thiobenzophenone),
4-(5-Amino-2-pyridylamino)-2-chloro-2'-methyl(thiobenzophenone),
2-Chloro-4-(4-isoquinolylamino)-2'-methyl(thiobenzophenone),
t-Butyl 5-(3-chloro-4-(2-methylthiobenzoyl)phenylamino)nicotinoate,
2-Chloro-2'-methyl-4-(4-methyl-3-pyridylamino)thiobenzophenone,
2-Chloro-2'-methyl-4-(6-methyl-3-pyridylamino)thiobenzophenone,
4-(5-Bromo-3-pyridylamino)-2-chloro-2'-methyl(thiobenzophenone),
4-(5-Carbonitrile-3-pyridylamino)-2-chloro-2'-methyl(thiobenzophenone),
4-(3-Bromo-2-pyridylamino)-2-chloro-2'-methyl(thiobenzophenone),
2-Chloro-2'-methyl-4-(8-quinolylamino)thiobenzophenone,
2-Chloro-4-(6-ethoxy-3-pyridylamino)-2'-methyl(thiobenzophenone),
4-(4-Bromo-1-isoquinolylamino)-2-chloro-2'-methyl(thiobenzophenone),
2-Chloro-2'-methyl-4-(2-methyl-5-trifluoromethyl-3-pyridylamino)thiobenzophenone,
2-Chloro-2'-methyl-4-(3-quinolylamino)thiobenzophenone,
2-Chloro-4-(4-ethoxy-3-pyridylamino)-2'-methyl(thiobenzophenone),
2-Chloro-4-(2-ethoxy-3-pyridylamino)-2'-methyl(thiobenzophenone),
2-Chloro-2'-methyl-4-(2-methyl-6-quinolylamino)thiobenzophenone,
2-Chloro-2'-methyl-4-(2-quinolylamino)thiobenzophenone,
2-Chloro-4-(7-chloro-4-quinolylamino)-2'-methyl(thiobenzophenone)
2-Chloro-2'-methyl-4-(4-quinolylamino)thiobenzophenone,
2-Chloro-2'-methyl-4-(1-methyl-7-indolylamino)thiobenzophenone
2-Chloro-2'-methyl-4-(1-methyl-5-indolylamino)thiobenzophenone,
2-Chloro-2',5'-dimethyl-4-(4-methyl-3-pyridylamino)thiobenzophenone,
2-Chloro-21,5'-dimethyl-4-(4-isoquinolylamino)thiobenzophenone,
2-Chloro-4-(4-isoquinolylamino)-2',4',5'-trimethyl(thiobenzophenone),
2,3'-Dichloro-2'-methyl-4-(4-methyl-3-pyridylamino)thiobenzophenone,
2-Fluoro-2'-methyl-4-(4-methyl-3-pyridylamino)thiobenzophenone,
2,4'-Dichloro-2'-methyl-4-(4-methyl-3-pyridylamino)thiobenzophenone,
2-Chloro-4'-fluoro-4-(4-isoquinolylamino)-2'-methyl(thiobenzophenone),
4'-n-Butyl-2-chloro-4-(4-isoquinolylamino)-2'-methyl(thiobenzophenone),
2-Chloro-4-(5-isoquinolylamino)-2'-methyl(thiobenzophenone), 2-Chloro-4-(4-isoquinolylamino)-4'-methoxy-2'-methyl(thiobenzophenone),
2-Fluoro-4-(4-isoquinolylamino)-4'-methoxy-2'-methyl(thiobenzophenone),
2,4'-Dichloro-2'-methyl-4-(1-methyl-7-indolylamino)thiobenzophenone,
2-Chloro-4-(1-methyl-7-indolylamino)-2',4',5'-trimethyl(thiobenzophenone),
2-Chloro-2',5'-dimethyl-4-(1-methyl-7-indoiylamino)thiobenzophenone,
2-Chloro-4-(3-ethoxy-4-isoquinolylamino)-2'-methyl(thiobenzophenone),
2-Chloro-4-(1-ethoxy-4-isoquinolylamino)-2'-methyl(thiobenzophenone),
4-(2-Benzoxazolylamino)-2-chloro-2'-methyl(thiobenzophenone),
4-(1-Methyl-2-benzimidazolylamino)-2-chloro-2'-methyl(thiobenzophenone),
4-(2-Benzothiazolylamino)-2-chloro-2'-methyl(thiobenzophenone), 2-Chloro-2'-methyl-4-(2-pyrimidylamino)
  thiobenzophenone,
2-Chloro-2'-methyl-4-(7-methyl-purin-6-ylamino)
  thiobenzophenone,
2-Chloro-2'-methyl-4-(2-methyl-5-benzothiazolylamino)
  thiobenzophenone,
2-Chloro-2'-methyl-4-(pyrazin-2-ylamino)
  thiobenzophenone, 2-Chloro-2'-methyl-4-(5-pyrimidylamino)thiobenzophenone and salts thereof with pharmaceutically acceptable acids, hydrates and solvates.

28. A compound according to claim 26 of formula Ib selected form the group consisting of:
  2-Chloro-2'-methyl-4-(4-pyridylamino)benzophenone oxime,
  2-Chloro-2'-methyl-4-(2-pyridylamino)benzophenone oxime,
  2-Chloro-2'-methyl-4-(5-nitro-2-pyridylamino) benzophenone oxime,
  4-(6-Amino-5-nitro-2-pyridylamino)-2-chloro-2'-methylbenzophenone oxime,
  6-Chloro-2-((3-chloro-4-((hydroxyimino) (2-methylphenyl)methyl))phenylamino)isonicotinic acid,
  4-(6-carbonitrile-2-pyridylamino)-2-chloro-2'-methylbenzophenone oxime,
  2-Chloro-2'-methyl-4-(3-pyridylamino)benzophenone oxime,
  2-Chloro-4-(5, 6-diamino-2-pyridylamino)-2'-methylbenzophenone oxime,
  2-Chloro-2'-methyl-4-(3-nitro-2-pyridylamino) benzophenone oxime,
  4-(3-Amino-2-pyridylamino)-2-chloro-2'-methylbenzophenone oxime,
  4-(5-Amino-2-pyridylamino)-2-chloro-2'-methylbenzophenone oxime,
  2-Chloro-4-(4-isoquinolylamino)-2'-methylbenzophenone oxime,
  t-Butyl 5-((3-chloro-4-((hydroxyimino) (2-methylphenyl)methyl))phenylamino)nicotinoate,
  2-Chloro-2'-methyl-4-(4-methyl-3-pyridylamino) benzophenone oxime,
  2-Chloro-2'-methyl-4-(6-methyl-3-pyridylamino) benzophenone oxime,
  4-(5-Bromo-3-pyridylamino)-2-chloro-2'-methylbenzophenone oxime,
  4-(5-Carbonitrile-3-pyridylamino)-2-chloro-2'-methylbenzophenone oxime,
  4-(3-Bromo-2-pyridylamino)-2-chloro-2'-methylbenzophenone oxime,
  2-Chloro-2'-methyl-4-(8-quinolylamino)benzophenone oxime,
  2-Chloro-4-(6-ethoxy-3-pyridylamino)-2'-methylbenzophenone oxime,
  4-(4-Bromo-1-isoquinolylamino)-2-chloro-2'-methylbenzophenone oxime,
  2-Chloro-2'-methyl-4-(2-methyl-5-trifluoromethyl-3-pyridylamino)benzophenone oxime,
  2-Chloro-2'-methyl-4-(3-quinolylamino)benzophenone oxime,
  2-Chloro-4-(4-ethoxy-3-pyridylamino)-2'-methylbenzophenone oxime,
  2-Chloro-4-(2-ethoxy-3-pyridylamino)-2'-methylbenzophenone oxime,
  2-Chloro-2'-methyl-4-(2-methyl-6-quinolylamino) benzophenone oxime,
  2-Chloro-2'-methyl-4-(2-quinolylamino)benzophenone oxime,
  2-Chloro-4-(7-chloro-4-quinolylamino)-2'-methylbenzophenone oxime,
  2-Chloro-2'-methyl-4-(4-quinolylamino)benzophenone oxime,
  2-Chloro-2'-methyl-4-(1-methyl-7-indolylamino) benzophenone oxime,
  2-Chloro-2'-methyl-4-(1-methyl-5-indolylamino) benzophenone oxime,
  2-Chloro-2',5'-dimethyl-4-(4-methyl-3-pyridylamino) benzophenone oxime,
  2-Chloro-2',5'-dimethyl-4-(4-isoquinolylamino) benzophenone oxime,
  2-Chloro-4-(4-isoquinolylamino)-2',4',5'-trimethylbenzophenone oxime,
  2,3'-Dichloro-2'-methyl-4-(4-methyl-3-pyridylamino) benzophenone oxime,
  2-Fluoro-2'-methyl-4-(4-methyl-3-pyridylamino) benzophenone oxime,
  2,4'-Dichloro-2'-methyl-4-(4-methyl-3-pyridylamino) benzophenone oxime,
  2-Chloro-4'-fluoro-4-(4-isoquinolylamino)-2'-methylbenzophenone oxime,
  4'-n-Butyl-2-chloro-4-(4-isoquinolylamino)-2'-methylbenzophenone oxime,
  2-Chloro-4-(5-isoquinolylamino)-2'-methylbenzophenone oxime,
  2-Chloro-4-(4-isoquinolylamino)-4'-methoxy-2'-methylbenzophenone oxime,
  2-Fluoro-4-(4-isoquinolylamino)-4'-methoxy-2'-methylbenzophenone oxime,
  2,4'-Dichloro-2'-methyl-4-(1-methyl-7-indolylamino) benzophenone oxime,
  2-Chloro-4-(1-methyl-7-indolylamino)-2',4',5'-trimethylbenzophenone oxime,
  2-Chloro-2',5'-dimethyl-4-(1-methyl-7-indolylamino) benzophenone oxime,
  2-Chloro-4-(3-ethoxy-4-isoquinolylamino)-2'-methylbenzophenone oxime,
  2-Chloro-4-(1-ethoxy-4-isoquinolylamino)-2'-methylbenzophenone oxime,
  4-(2-Benzoxazolylamino)-2-chloro-2'-methylbenzophenone oxime,
  4-(1-Methyl-2-benzimidazolylamino)-2-chloro-2'-methylbenzophenone oxime,
  4-(2-Benzothiazolylamino)-2-chloro-2'-methylbenzophenone oxime,
  2-Chloro-2'-methyl-4-(2-pyrimidylamino)benzophenone oxime,
  2-Chloro-2'-methyl-4-(7-methyl-purin-6-ylamino) benzophenone oxime,
  2-Chloro-2'-methyl-4-(2-methyl-5-benzothiazolylamino) benzophenone oxime,
  2-Chloro-2'-methyl-4-(pyrazin-2-ylamino)benzophenone oxime,
  2-Chloro-2'-methyl-4-(5-pyrimidylamino)benzophenone oxime, and salts thereof with pharmaceutically acceptable acids, hydrates and solvates.

29. A pharmaceutical composition containing as an active component a compound of formula I according to claim 1 together with a pharmaceutically acceptable excipient or carrier.

30. A composition according to claim 29 further comprising a second active ingredient optionally selected from the group consisting of glucocorticoids, vitamin D or vitamin D analogues, anti-histamines, platelet activating factor (PAF) antagonists, anticolinergic agents, methyl xanthines, β-adrenergic agents, salicylates, indomethacin, flufenamate, naproxen, timegadine, gold salts, penicillamine, serum cholesterol-reducing agents, retinoids, zinc salts, and salicylazosulfapyridin.

31. A composition according to claim 29 in unit dosage form containing between 0.05 and 1000 mg of the active ingredient.

32. A method for the treatment or prophylaxis of inflammatory diseases or conditions, the method comprising administering, to a patient in need thereof, an effective amount of one or more compounds of general formula I according to claim 1.

33. The method of claim 32 further comprising administering a second active component selected from the group consisting of glucocorticoids, vitamin D's, anti-histamines, platelet activating factor (PAF) antagonists, anticolinergic agents, methyl xanthines, β-adrenergic agents, salicylates, indomethacin, flufenamate, naproxen, timegadine, gold salts, penicillamine, serum cholesterol-reducing agents, retinoids, zinc salts, and salicylazosulfapyridin.

34. The method of claim 32, wherein the disease or condition is selected from the group consisting of asthma and allergy.

35. The method of claim 32, wherein the disease or condition is selected from the group consisting of arthritis, including rheumatoid arthritis, osteoarthritis and spondyloarthritis, gout, atherosclerosis, inflammatory bowel disease, Crohn's disease, uveitis, sepsis and septic shock.

36. The method of claim 32, wherein the disease or condition is a proliferative and/or inflammatory skin disorder.

37. A method for the treatment and/or prophylaxis of osteoporosis, the method comprising administering to a patient in need thereof an effective amount of one or more compounds of formula I according to claim 1.

38. A method for the treatment of AIDS related diseases, the method comprising administering to a patient in need thereof an effective amount of one or more compounds of formula I according to claim 1.

39. The method of any one of claims 32–38 comprising administering to a patient in need of systemic treatment a dose of from 0.01 to 400 mg/kg body weight one or more times daily of a compound of formula I according to claim 1.

40. A compound according to claim 2, wherein $R_1$ represents a substituent selected from the group consisting of fluoro, chloro, bromo, hydroxy, trifluoromethyl, amino, $(C_1-C_3)$alkyl, $(C_2-C_3)$ alkenyl, $(C_1-C_3)$alkoxy, $(C_1-C_3)$alkoxycarbonyl, cyano, and $-CONH_2$.

41. A compound according to claim 3, wherein $R_2$ represents one or more, same or different substituents selected from the group consisting of hydrogen, fluoro, chloro, bromo, hydroxy, trifluoromethyl, amino, $(C_1-C_3)$alkyl, $(C_2-C_3)$alkenyl, $(C_1-C_3)$alkoxy, $(C_1-C_3)$alkoxycarbonyl, cyano, and $-CONH_2$.

42. A compound according to claim 4, wherein $R_3$ represents one or more, same or different substituents selected from the group consisting of hydrogen, fluoro, chloro, bromo, hydroxy, trifluoromethyl, amino, $(C_1-C_3)$alkyl, $(C_2-C_3)$alkenyl, and $(C_1-C_3)$alkoxy.

43. A compound according to claim 5, wherein $R_4$ represents hydrogen, $(C_1-C_4)$alkyl or $(C_2-C_4)$alkenyl.

44. A compound according to claim 8, wherein X represents oxygen or NH.

45. A compound according to claim 10, wherein $R_8$ represents alkyl.

46. A compound according to claim 22, wherein $R_1$ represents fluoro or chloro.

47. A compound according to claim 22, wherein $R_2$ represents hydrogen, $(C_1-C_3)$alkyl, methoxy or ethoxy.

48. A compound according to claim 47, wherein $R_1$ represents fluoro or chloro.

49. The method of claim 36, wherein the disease or condition is selected from the group consisting of psoriasis, atopic dermatitis and acne vulgaris.

50. The method of claim 39, wherein the dose is a dose from 0.1 to 100 mg/kg body weight.

* * * * *